US012778712B2

(12) United States Patent
Gera et al.

(10) Patent No.: US 12,778,712 B2
(45) Date of Patent: Nov. 3, 2026

(54) ROTATING MARKER AND ADAPTER FOR IMAGE-GUIDED SURGERY

(71) Applicant: AUGMEDICS LTD., Yokneam Illit (IL)

(72) Inventors: Tomer Gera, Kfar-Tavor (IL); Nissan Elimelech, Beerotaim (IL)

(73) Assignee: Augmedics Ltd., Yokneam Illit (IL)

( * ) Notice: Subject to any disclaimer, the term of this patent is extended or adjusted under 35 U.S.C. 154(b) by 277 days.

(21) Appl. No.: 18/291,731

(22) PCT Filed: Jul. 28, 2022

(86) PCT No.: PCT/IB2022/056986
§ 371 (c)(1),
(2) Date: Jan. 24, 2024

(87) PCT Pub. No.: WO2023/007418
PCT Pub. Date: Feb. 2, 2023

(65) Prior Publication Data

US 2025/0090266 A1 Mar. 20, 2025

Related U.S. Application Data

(63) Continuation-in-part of application No. 17/388,064, filed on Jul. 29, 2021, now Pat. No. 12,150,821.

(51) Int. Cl.
*A61B 90/00* (2016.01)
*A61B 34/20* (2016.01)

(52) U.S. Cl.
CPC .............. *A61B 90/39* (2016.02); *A61B 34/20* (2016.02); *A61B 90/361* (2016.02);
(Continued)

(58) Field of Classification Search
CPC ............ A61B 2090/3983; A61B 90/39; A61B 2090/3916; A61B 2090/3991;
(Continued)

(56) References Cited

U.S. PATENT DOCUMENTS 3,101,715 A 8/1963 Glassman
3,690,776 A 9/1972 Zaporoshan
(Continued)

FOREIGN PATENT DOCUMENTS

CA 3022448 A1 2/2018
CA 3034314 A1 2/2018
(Continued)

OTHER PUBLICATIONS

16 Augmented Reality Glasses of 2021 (with Features), in Back to News, Dated May 6, 2022, accessed at https://web.archive. org/web/20221127195438/https://circuitstream.com/blog/16-augmented-reality-glasses-of-2021-with-features-breakdowns/.
(Continued)

*Primary Examiner* — Anhtuan T Nguyen
*Assistant Examiner* — Tommy T Ly
(74) *Attorney, Agent, or Firm* — Dinsmore & Shohl LLP

(57) ABSTRACT

A patient marker (52) couples to an anchoring device (34) via a base (44) having a base axis, base connections and a first indicator (168). The marker includes: an adapter (40) having a first surface with connections configured to mate with the base connections, and a second surface with connections congruent with the base connections, and at least one second indicator (172). The marker includes an alignment target (48), having a target region (74) with an alignment pattern, and a socket (78) connected to the target region with socket connections congruent with the first surface connections. In a first configuration the socket couples to the base by mating the first surface connections with the base connections and mating the socket connections with the second surface connections. In a second configuration, the socket fits onto the base by mating the socket connections with the base connections.

10 Claims, 10 Drawing Sheets

(52) U.S. Cl.
CPC ................. *A61B 2034/2055* (2016.02); *A61B 2090/3983* (2016.02); *A61B 2090/3991* (2016.02)

(58) Field of Classification Search
CPC .... A61B 2034/2055; A61B 2034/2065; A61B 2034/207
See application file for complete search history.

(56) References Cited

U.S. PATENT DOCUMENTS

| | | | |
|---|---|---|---|
| 4,459,358 | A | 7/1984 | Berke |
| 4,711,512 | A | 12/1987 | Upatnieks |
| 4,863,238 | A | 9/1989 | Brewster |
| 4,944,739 | A | 7/1990 | Torre |
| 5,100,420 | A | 3/1992 | Green et al. |
| 5,147,365 | A | 9/1992 | Whitlock et al. |
| 5,357,292 | A | 10/1994 | Wiedner |
| 5,410,802 | A | 5/1995 | Buckley |
| 5,441,042 | A | 8/1995 | Putman |
| 5,442,146 | A | 8/1995 | Bell et al. |
| 5,510,832 | A | 4/1996 | Garcia |
| D370,309 | S | 5/1996 | Stucky |
| 5,620,188 | A | 4/1997 | Mccurry et al. |
| 5,636,255 | A | 6/1997 | Ellis |
| 5,665,092 | A | 9/1997 | Mangiardi et al. |
| 5,743,731 | A | 4/1998 | Lares et al. |
| 5,771,121 | A | 6/1998 | Hentschke |
| 5,792,046 | A | 8/1998 | Dobrovolny |
| 5,841,507 | A | 11/1998 | Barnes |
| 6,006,126 | A | 12/1999 | Cosman |
| 6,038,467 | A | 3/2000 | De Bliek et al. |
| 6,125,164 | A | 9/2000 | Murphy et al. |
| 6,138,530 | A | 10/2000 | McClure |
| 6,147,805 | A | 11/2000 | Fergason |
| 6,227,667 | B1 | 5/2001 | Halldorsson et al. |
| 6,256,529 | B1 | 7/2001 | Holupka et al. |
| 6,285,505 | B1 | 9/2001 | Melville et al. |
| 6,314,310 | B1 | 11/2001 | Ben-Haim et al. |
| 6,349,001 | B1 | 2/2002 | Spitzer |
| 6,444,192 | B1 | 9/2002 | Mattrey |
| 6,447,503 | B1 | 9/2002 | Wynne et al. |
| 6,449,090 | B1 | 9/2002 | Omar et al. |
| 6,456,405 | B2 | 9/2002 | Horikoshi et al. |
| 6,456,868 | B2 | 9/2002 | Saito et al. |
| 6,474,159 | B1 | 11/2002 | Foxlin et al. |
| 6,518,939 | B1 | 2/2003 | Kikuchi |
| 6,527,777 | B2 | 3/2003 | Justin |
| 6,529,331 | B2 | 3/2003 | Massof et al. |
| 6,549,645 | B1 | 4/2003 | Oikawa et al. |
| 6,578,962 | B1 | 6/2003 | Amir et al. |
| 6,609,022 | B2 | 8/2003 | Vilsmeier et al. |
| 6,610,009 | B2 | 8/2003 | Person |
| D480,476 | S | 10/2003 | Martinson et al. |
| 6,659,611 | B2 | 12/2003 | Amir et al. |
| 6,675,040 | B1 | 1/2004 | Cosman |
| 6,683,584 | B2 | 1/2004 | Ronzani et al. |
| 6,690,964 | B2 | 2/2004 | Bieger et al. |
| 6,714,810 | B2 | 3/2004 | Grzeszczuk et al. |
| 6,737,425 | B1 | 5/2004 | Yamamoto et al. |
| 6,740,882 | B2 | 5/2004 | Weinberg |
| 6,757,068 | B2 | 6/2004 | Foxlin |
| 6,759,200 | B1 | 7/2004 | Stanton, Jr. |
| 6,847,336 | B1 | 1/2005 | Lemelson et al. |
| 6,856,324 | B2 | 2/2005 | Sauer et al. |
| 6,856,826 | B2 | 2/2005 | Seeley et al. |
| 6,891,518 | B2 | 5/2005 | Sauer et al. |
| 6,900,777 | B1 | 5/2005 | Hebert et al. |
| 6,919,867 | B2 | 7/2005 | Sauer |
| 6,921,167 | B2 | 7/2005 | Nagata |
| 6,966,668 | B2 | 11/2005 | Cugini et al. |
| 6,980,849 | B2 | 12/2005 | Sasso |
| 6,993,374 | B2 | 1/2006 | Sasso |
| 6,997,552 | B1 | 2/2006 | Hung |
| 6,999,239 | B1 | 2/2006 | Martins et al. |
| 7,000,262 | B2 | 2/2006 | Bielefeld |
| 7,035,371 | B2 | 4/2006 | Boese et al. |
| 7,043,961 | B2 | 5/2006 | Pandey et al. |
| 7,072,435 | B2 | 7/2006 | Metz et al. |
| 7,103,233 | B2 | 9/2006 | Stearns |
| 7,107,091 | B2 | 9/2006 | Jutras et al. |
| 7,112,656 | B2 | 9/2006 | Desnoyers et al. |
| 7,141,812 | B2 | 11/2006 | Appleby et al. |
| 7,157,459 | B2 | 1/2007 | Ohta et al. |
| 7,169,785 | B2 | 1/2007 | Timmer et al. |
| 7,171,255 | B2 | 1/2007 | Holupka et al. |
| 7,176,936 | B2 | 2/2007 | Sauer et al. |
| 7,187,792 | B2 | 3/2007 | Fu et al. |
| 7,190,331 | B2 | 3/2007 | Genc et al. |
| 7,194,295 | B2 | 3/2007 | Vilsmeier |
| 7,215,322 | B2 | 5/2007 | Genc et al. |
| 7,229,078 | B2 | 6/2007 | Lechot |
| 7,231,076 | B2 | 6/2007 | Fu et al. |
| 7,235,076 | B2 | 6/2007 | Pacheco |
| 7,239,330 | B2 | 7/2007 | Sauer et al. |
| 7,241,292 | B2 | 7/2007 | Hooven |
| 7,259,266 | B2 | 8/2007 | Carter et al. |
| 7,260,426 | B2 | 8/2007 | Schweikard et al. |
| 7,269,192 | B2 | 9/2007 | Hayashi |
| 7,281,826 | B2 | 10/2007 | Huang |
| 7,315,636 | B2 | 1/2008 | Kuduvalli |
| 7,320,556 | B2 | 1/2008 | Vagn-Erik |
| 7,330,578 | B2 | 2/2008 | Wang et al. |
| 7,359,535 | B2 | 4/2008 | Salla et al. |
| 7,364,314 | B2 | 4/2008 | Nilsen et al. |
| 7,366,934 | B1 | 4/2008 | Narayan et al. |
| 7,379,077 | B2 | 5/2008 | Bani-Hashemi et al. |
| 7,431,453 | B2 | 10/2008 | Hogan |
| 7,435,219 | B2 | 10/2008 | Kim |
| 7,450,743 | B2 | 11/2008 | Sundar et al. |
| 7,458,977 | B2 | 12/2008 | Mcginley et al. |
| 7,462,852 | B2 | 12/2008 | Appleby et al. |
| 7,493,153 | B2 | 2/2009 | Ahmed et al. |
| 7,505,617 | B2 | 3/2009 | Fu et al. |
| 7,507,968 | B2 | 3/2009 | Wollenweber et al. |
| 7,518,136 | B2 | 4/2009 | Appleby et al. |
| 7,525,735 | B2 | 4/2009 | Sottilare et al. |
| D592,691 | S | 5/2009 | Chang |
| D592,692 | S | 5/2009 | Chang |
| D592,693 | S | 5/2009 | Chang |
| 7,536,216 | B2 | 5/2009 | Geiger et al. |
| 7,542,791 | B2 | 6/2009 | Mire et al. |
| 7,556,428 | B2 | 7/2009 | Sukovic et al. |
| 7,557,824 | B2 | 7/2009 | Holliman |
| 7,563,228 | B2 | 7/2009 | Ma et al. |
| 7,567,834 | B2 | 7/2009 | Clayton et al. |
| 7,570,791 | B2 | 8/2009 | Frank et al. |
| 7,586,686 | B1 | 9/2009 | Hall |
| D602,620 | S | 10/2009 | Cristoforo |
| 7,605,826 | B2 | 10/2009 | Sauer |
| 7,606,613 | B2 | 10/2009 | Simon et al. |
| 7,607,775 | B2 | 10/2009 | Hermanson et al. |
| 7,620,223 | B2 | 11/2009 | Xu et al. |
| 7,623,902 | B2 | 11/2009 | Pacheco |
| 7,627,085 | B2 | 12/2009 | Boyden et al. |
| 7,630,753 | B2 | 12/2009 | Simon et al. |
| 7,633,501 | B2 | 12/2009 | Wood et al. |
| 7,645,050 | B2 | 1/2010 | Wilt et al. |
| 7,653,226 | B2 | 1/2010 | Guhring et al. |
| 7,657,075 | B2 | 2/2010 | Viswanathan |
| 7,689,019 | B2 | 3/2010 | Boese et al. |
| 7,689,042 | B2 | 3/2010 | Brunner et al. |
| 7,689,320 | B2 | 3/2010 | Prisco et al. |
| 7,699,486 | B1 | 4/2010 | Beiner |
| 7,699,793 | B2 | 4/2010 | Goette et al. |
| 7,719,769 | B2 | 5/2010 | Sugihara et al. |
| D617,825 | S | 6/2010 | Chang |
| 7,734,327 | B2 | 6/2010 | Colquhoun |
| D619,285 | S | 7/2010 | Cristoforo |
| 7,751,865 | B2 | 7/2010 | Jascob et al. |
| 7,758,204 | B2 | 7/2010 | Klipstein et al. |
| 7,768,702 | B2 | 8/2010 | Hirose et al. |
| 7,769,236 | B2 | 8/2010 | Fiala |
| 7,773,074 | B2 | 8/2010 | Arenson et al. |

(56) References Cited

U.S. PATENT DOCUMENTS

| | | | |
|---|---|---|---|
| 7,774,044 | B2 | 8/2010 | Sauer et al. |
| 7,822,483 | B2 | 10/2010 | Stone et al. |
| D628,307 | S | 11/2010 | Krause-Bonte |
| 7,826,902 | B2 | 11/2010 | Stone et al. |
| 7,831,073 | B2 | 11/2010 | Fu et al. |
| 7,831,096 | B2 | 11/2010 | Williamson, Jr. |
| 7,835,778 | B2 | 11/2010 | Foley et al. |
| 7,835,784 | B2 | 11/2010 | Mire et al. |
| 7,837,987 | B2 | 11/2010 | Shi et al. |
| 7,840,093 | B2 | 11/2010 | Fu et al. |
| 7,840,253 | B2 | 11/2010 | Tremblay et al. |
| 7,840,256 | B2 | 11/2010 | Lakin et al. |
| 7,853,305 | B2 | 12/2010 | Simon et al. |
| 7,854,705 | B2 | 12/2010 | Pawluczyk et al. |
| 7,857,271 | B2 | 12/2010 | Lees |
| 7,860,282 | B2 | 12/2010 | Boese et al. |
| D630,766 | S | 1/2011 | Harbin |
| 7,865,269 | B2 | 1/2011 | Prisco et al. |
| 7,874,686 | B2 | 1/2011 | Rossner et al. |
| 7,881,770 | B2 | 2/2011 | Melkent et al. |
| 7,893,413 | B1 | 2/2011 | Appleby et al. |
| 7,894,649 | B2 | 2/2011 | Fu et al. |
| 7,920,162 | B2 | 4/2011 | Masini et al. |
| 7,922,391 | B2 | 4/2011 | Essenreiter et al. |
| 7,938,553 | B1 | 5/2011 | Beiner |
| 7,945,310 | B2 | 5/2011 | Gattani et al. |
| 7,953,471 | B2 | 5/2011 | Clayton et al. |
| 7,969,383 | B2 | 6/2011 | Eberl et al. |
| 7,974,677 | B2 | 7/2011 | Mire et al. |
| 7,985,756 | B2 | 7/2011 | Barlow et al. |
| 7,991,557 | B2 | 8/2011 | Liew et al. |
| 7,993,353 | B2 | 8/2011 | Roner et al. |
| 7,996,064 | B2 | 8/2011 | Simon et al. |
| 8,004,524 | B2 | 8/2011 | Deinzer |
| 8,021,300 | B2 | 9/2011 | Ma et al. |
| 8,022,984 | B2 | 9/2011 | Cheong et al. |
| 8,045,266 | B2 | 10/2011 | Nakamura |
| 8,060,181 | B2 | 11/2011 | Rodriguez et al. |
| 8,068,581 | B2 | 11/2011 | Boese et al. |
| 8,068,896 | B2 | 11/2011 | Daghighian et al. |
| 8,077,943 | B2 | 12/2011 | Williams et al. |
| 8,079,957 | B2 | 12/2011 | Ma et al. |
| 8,081,812 | B2 | 12/2011 | Kreiser |
| 8,085,075 | B2 | 12/2011 | Huffman et al. |
| 8,085,897 | B2 | 12/2011 | Morton |
| 8,090,175 | B2 | 1/2012 | Fu et al. |
| 8,092,400 | B2 | 1/2012 | Warkentine et al. |
| 8,108,072 | B2 | 1/2012 | Zhao et al. |
| 8,112,292 | B2 | 2/2012 | Simon |
| 8,116,847 | B2 | 2/2012 | Gattani et al. |
| 8,120,847 | B2 | 2/2012 | Chang |
| 8,121,255 | B2 | 2/2012 | Sugiyama |
| 8,155,479 | B2 | 4/2012 | Hoffman et al. |
| 8,180,132 | B2 | 5/2012 | Gorges et al. |
| 8,180,429 | B2 | 5/2012 | Sasso |
| 8,208,599 | B2 | 6/2012 | Ye et al. |
| 8,216,211 | B2 | 7/2012 | Mathis et al. |
| 8,221,402 | B2 | 7/2012 | Francischelli et al. |
| 8,239,001 | B2 | 8/2012 | Verard et al. |
| 8,244,012 | B2 | 8/2012 | Liang et al. |
| 8,253,778 | B2 | 8/2012 | Atsushi |
| 8,271,069 | B2 | 9/2012 | Jascob et al. |
| 8,280,491 | B2 | 10/2012 | Kuduvalli et al. |
| 8,285,021 | B2 | 10/2012 | Boese et al. |
| 8,300,315 | B2 | 10/2012 | Kobayashi |
| 8,305,685 | B2 | 11/2012 | Heine et al. |
| 8,306,305 | B2 | 11/2012 | Porat et al. |
| 8,309,932 | B2 | 11/2012 | Haselman et al. |
| 8,317,320 | B2 | 11/2012 | Huang |
| 8,328,815 | B2 | 12/2012 | Farr et al. |
| 8,335,553 | B2 | 12/2012 | Rubner et al. |
| 8,335,557 | B2 | 12/2012 | Maschke |
| 8,340,379 | B2 | 12/2012 | Razzaque et al. |
| 8,369,925 | B2 | 2/2013 | Giesel et al. |
| 8,386,022 | B2 | 2/2013 | Jutras et al. |
| 8,394,144 | B2 | 3/2013 | Zehavi et al. |
| 8,398,541 | B2 | 3/2013 | Dimaio et al. |
| 8,444,266 | B2 | 5/2013 | Waters |
| 8,457,719 | B2 | 6/2013 | Moctezuma De La Barrera et al. |
| 8,467,851 | B2 | 6/2013 | Mire et al. |
| 8,469,902 | B2 | 6/2013 | Dick et al. |
| 8,475,470 | B2 | 7/2013 | Von Jako |
| 8,494,612 | B2 | 7/2013 | Vetter et al. |
| 8,509,503 | B2 | 8/2013 | Nahum et al. |
| 8,511,827 | B2 | 8/2013 | Hua et al. |
| 8,531,394 | B2 | 9/2013 | Maltz |
| 8,540,364 | B2 | 9/2013 | Waters |
| 8,545,012 | B2 | 10/2013 | Waters |
| 8,548,567 | B2 | 10/2013 | Maschke et al. |
| 8,556,883 | B2 | 10/2013 | Saleh |
| 8,559,596 | B2 | 10/2013 | Thomson et al. |
| 8,567,945 | B2 | 10/2013 | Waters |
| 8,571,353 | B2 | 10/2013 | Watanabe |
| 8,585,598 | B2 | 11/2013 | Razzaque et al. |
| 8,600,001 | B2 | 12/2013 | Schweizer |
| 8,600,477 | B2 | 12/2013 | Beyar et al. |
| 8,605,199 | B2 | 12/2013 | Imai |
| 8,611,988 | B2 | 12/2013 | Miyamoto |
| 8,612,024 | B2 | 12/2013 | Stone et al. |
| 8,634,897 | B2 | 1/2014 | Simon et al. |
| 8,641,621 | B2 | 2/2014 | Razzaque et al. |
| 8,643,950 | B2 | 2/2014 | König |
| 8,644,907 | B2 | 2/2014 | Hartmann et al. |
| 8,674,902 | B2 | 3/2014 | Park et al. |
| 8,686,923 | B2 | 4/2014 | Eberl et al. |
| 8,690,581 | B2 | 4/2014 | Ruf et al. |
| 8,690,776 | B2 | 4/2014 | Razzaque et al. |
| 8,692,845 | B2 | 4/2014 | Fedorovskaya et al. |
| 8,693,632 | B2 | 4/2014 | Allison |
| 8,694,075 | B2 | 4/2014 | Groszmann et al. |
| 8,699,765 | B2 | 4/2014 | Hao et al. |
| 8,705,829 | B2 | 4/2014 | Frank et al. |
| 8,737,708 | B2 | 5/2014 | Hartmann et al. |
| 8,746,887 | B2 | 6/2014 | Shestak et al. |
| 8,764,025 | B1 | 7/2014 | Gao |
| 8,784,450 | B2 | 7/2014 | Moskowitz et al. |
| 8,786,689 | B1 | 7/2014 | Liu |
| D710,545 | S | 8/2014 | Wu |
| D710,546 | S | 8/2014 | Wu |
| 8,827,934 | B2 | 9/2014 | Chopra et al. |
| 8,831,706 | B2 | 9/2014 | Fu et al. |
| 8,836,768 | B1 | 9/2014 | Rafii et al. |
| 8,838,199 | B2 | 9/2014 | Simon et al. |
| 8,848,977 | B2 | 9/2014 | Bammer et al. |
| 8,855,395 | B2 | 10/2014 | Baturin et al. |
| 8,878,900 | B2 | 11/2014 | Yang et al. |
| 8,879,815 | B2 | 11/2014 | Miao et al. |
| 8,885,177 | B2 | 11/2014 | Ben-Yishai et al. |
| 8,890,772 | B2 | 11/2014 | Woo et al. |
| 8,890,773 | B1 | 11/2014 | Pederson |
| 8,890,943 | B2 | 11/2014 | Lee et al. |
| 8,897,514 | B2 | 11/2014 | Feikas et al. |
| 8,900,131 | B2 | 12/2014 | Chopra et al. |
| 8,903,150 | B2 | 12/2014 | Star-Lack et al. |
| 8,908,952 | B2 | 12/2014 | Isaacs et al. |
| 8,911,358 | B2 | 12/2014 | Koninckx et al. |
| 8,917,268 | B2 | 12/2014 | Johnsen et al. |
| 8,920,776 | B2 | 12/2014 | Gaiger et al. |
| 8,922,589 | B2 | 12/2014 | Laor |
| 8,941,559 | B2 | 1/2015 | Bar-Zeev et al. |
| 8,942,455 | B2 | 1/2015 | Chou et al. |
| 8,950,877 | B2 | 2/2015 | Northey et al. |
| 8,953,246 | B2 | 2/2015 | Koenig |
| 8,965,583 | B2 | 2/2015 | Ortmaier et al. |
| 8,969,829 | B2 | 3/2015 | Wollenweber et al. |
| 8,989,349 | B2 | 3/2015 | Thomson et al. |
| 8,992,580 | B2 | 3/2015 | Bar et al. |
| 8,994,729 | B2 | 3/2015 | Nakamura |
| 8,994,795 | B2 | 3/2015 | Oh |
| 9,004,711 | B2 | 4/2015 | Gerolemou |
| 9,005,211 | B2 | 4/2015 | Brundobler et al. |
| 9,011,441 | B2 | 4/2015 | Bertagnoli et al. |
| 9,057,759 | B2 | 6/2015 | Klingenbeck et al. |
| 9,060,757 | B2 | 6/2015 | Lawson et al. |

(56) References Cited

U.S. PATENT DOCUMENTS 9,066,751 B2 6/2015 Sasso
9,081,436 B1 7/2015 Berme et al.
9,084,635 B2 7/2015 Nuckley et al.
9,085,643 B2 7/2015 Svanborg et al.
9,087,471 B2 7/2015 Miao
9,100,643 B2 8/2015 Mcdowall et al.
9,101,394 B2 8/2015 Arata et al.
9,104,902 B2 8/2015 Xu et al.
9,111,175 B2 8/2015 Strommer et al.
9,123,155 B2 9/2015 Cunningham et al.
9,125,556 B2 9/2015 Zehavi et al.
9,129,054 B2 9/2015 Nawana et al.
9,129,372 B2 9/2015 Kriston et al.
9,132,361 B2 9/2015 Smithwick
9,135,706 B2 9/2015 Zagorchev et al.
9,141,873 B2 9/2015 Takemoto
9,142,020 B2 9/2015 Deguise et al.
9,149,317 B2 10/2015 Arthur et al.
9,165,203 B2 10/2015 McCarthy
9,165,362 B2 10/2015 Siewerdsen et al.
9,179,984 B2 11/2015 Teichman et al.
D746,354 S 12/2015 Chang
9,208,916 B2 12/2015 Appleby et al.
9,220,573 B2 12/2015 Kendrick et al.
9,225,895 B2 12/2015 Kozinski
9,232,982 B2 1/2016 Soler et al.
9,235,934 B2 1/2016 Mandella et al.
9,240,046 B2 1/2016 Carrell et al.
9,244,278 B2 1/2016 Sugiyama et al.
9,247,240 B2 1/2016 Park et al.
9,259,192 B2 2/2016 Ishihara
9,265,572 B2 2/2016 Fuchs et al.
9,269,192 B2 2/2016 Kobayashi
9,283,052 B2 3/2016 Rodriguez Ponce
9,286,730 B2 3/2016 Bar-Zeev et al.
9,289,267 B2 3/2016 Sauer et al.
9,294,222 B2 3/2016 Proctor, Jr.
9,300,949 B2 3/2016 Ahearn
9,305,354 B2 4/2016 Burlon et al.
9,310,591 B2 4/2016 Hua et al.
9,320,474 B2 4/2016 Demri et al.
9,323,055 B2 4/2016 Baillot
9,330,477 B2 5/2016 Rappel
9,335,547 B2 5/2016 Takano et al.
9,335,567 B2 5/2016 Nakamura
9,341,704 B2 5/2016 Picard et al.
9,344,686 B2 5/2016 Moharir
9,349,066 B2 5/2016 Koo et al.
9,349,520 B2 5/2016 Demetriou et al.
9,364,294 B2 6/2016 Razzaque et al.
9,370,332 B2 6/2016 Paladini et al.
9,373,166 B2 6/2016 Azar
9,375,639 B2 6/2016 Kobayashi et al.
9,378,558 B2 6/2016 Kajiwara et al.
9,380,287 B2 6/2016 Nistico et al.
9,387,008 B2 7/2016 Sarvestani et al.
9,392,129 B2 7/2016 Simmons
9,395,542 B2 7/2016 Tilleman et al.
9,398,936 B2 7/2016 Razzaque et al.
9,400,384 B2 7/2016 Griffith
9,414,041 B2 8/2016 Ko et al.
9,424,611 B2 8/2016 Kanjirathinkal et al.
9,424,641 B2 8/2016 Wiemker et al.
9,427,286 B2 8/2016 Siewerdsen et al.
9,438,894 B2 9/2016 Park et al.
9,443,488 B2 9/2016 Borenstein et al.
9,453,804 B2 9/2016 Tahtali
9,456,878 B2 10/2016 Macfarlane et al.
9,465,235 B2 10/2016 Chang
9,468,373 B2 10/2016 Larsen
9,470,908 B1 10/2016 Frankel et al.
9,473,766 B2 10/2016 Douglas et al.
9,492,222 B2 11/2016 Singh
9,495,585 B2 11/2016 Bicer et al.
9,498,132 B2 11/2016 Maier-Hein et al.
9,498,231 B2 11/2016 Haider et al.
9,499,999 B2 11/2016 Nanqing
9,507,155 B2 11/2016 Morimoto
9,513,495 B2 12/2016 Waters
9,521,966 B2 12/2016 Schwartz
9,526,443 B1 12/2016 Berme et al.
9,530,382 B2 12/2016 Simmons
9,532,846 B2 1/2017 Nakamura
9,532,849 B2 1/2017 Anderson et al.
9,533,407 B1 1/2017 Ragner
9,538,962 B1 1/2017 Hannaford et al.
9,545,233 B2 1/2017 Sirpad et al.
9,546,779 B2 1/2017 Rementer
9,547,174 B2 1/2017 Gao et al.
9,547,940 B1 1/2017 Sun et al.
9,557,566 B2 1/2017 Fujimaki
9,560,318 B2 1/2017 Reina et al.
9,561,095 B1 2/2017 Nguyen et al.
9,561,446 B2 2/2017 Brecher
9,565,415 B2 2/2017 Zhang et al.
9,572,661 B2 2/2017 Robin et al.
9,576,398 B1 2/2017 Zehner et al.
9,576,556 B2 2/2017 Simmons
9,581,822 B2 2/2017 Morimoto
9,610,056 B2 4/2017 Lavallee et al.
9,612,657 B2 4/2017 Bertram et al.
9,626,936 B2 4/2017 Bell
9,629,595 B2 4/2017 Walker et al.
9,633,431 B2 4/2017 Merlet
9,645,395 B2 5/2017 Bolas et al.
9,646,423 B1 5/2017 Sun et al.
9,672,597 B2 6/2017 Amiot et al.
9,672,607 B2 6/2017 Demri et al.
9,672,640 B2 6/2017 Kleiner
9,675,306 B2 6/2017 Morton
9,675,319 B1 6/2017 Razzaque et al.
9,684,980 B2 6/2017 Royalty et al.
9,690,119 B2 6/2017 Garofolo et al.
RE46,463 E 7/2017 Fienbloom et al.
9,693,748 B2 7/2017 Rai et al.
9,710,968 B2 7/2017 Dillavou et al.
9,713,502 B2 7/2017 Finkman et al.
9,724,119 B2 8/2017 Hissong et al.
9,724,165 B2 8/2017 Arata et al.
9,726,888 B2 8/2017 Giartosio et al.
9,728,006 B2 8/2017 Varga
9,729,831 B2 8/2017 Birnkrant et al.
9,746,739 B2 8/2017 Alton et al.
9,757,034 B2 9/2017 Desjardins et al.
9,757,087 B2 9/2017 Simon et al.
9,766,441 B2 9/2017 Rappel
9,766,459 B2 9/2017 Alton et al.
9,767,608 B2 9/2017 Lee et al.
9,770,203 B1 9/2017 Berme et al.
9,772,102 B1 9/2017 Ferguson
9,772,495 B2 9/2017 Tam et al.
9,791,138 B1 10/2017 Feinbloom et al.
9,800,995 B2 10/2017 Libin et al.
9,805,504 B2 10/2017 Zhang et al.
9,808,148 B2 11/2017 Miller et al.
9,839,448 B2 12/2017 Reckling et al.
9,844,413 B2 12/2017 Daon et al.
9,851,080 B2 12/2017 Wilt et al.
9,858,663 B2 1/2018 Penney et al.
9,861,446 B2 1/2018 Lang
9,864,214 B2 1/2018 Fass
9,872,733 B2 1/2018 Shoham et al.
9,875,544 B2 1/2018 Rai et al.
9,877,642 B2 1/2018 Duret
9,885,465 B2 2/2018 Nguyen
9,886,552 B2 2/2018 Dillavou et al.
9,886,760 B2 2/2018 Liu et al.
9,892,564 B1 2/2018 Cvetko et al.
9,898,866 B2 2/2018 Fuchs et al.
9,901,414 B2 2/2018 Lively et al.
9,911,187 B2 3/2018 Steinle et al.
9,911,236 B2 3/2018 Bar et al.
9,927,611 B2 3/2018 Rudy et al.
9,928,629 B2 3/2018 Benishti et al.

(56) References Cited

U.S. PATENT DOCUMENTS 9,940,750 B2 4/2018 Dillavou et al.
9,943,374 B2 4/2018 Merritt et al.
9,947,110 B2 4/2018 Haimerl
9,952,664 B2 4/2018 Border et al.
9,956,054 B2 5/2018 Aguirre-Valencia
9,958,674 B2 5/2018 Border
9,959,620 B2 5/2018 Merlet
9,959,629 B2 5/2018 Dillavou et al.
9,965,681 B2 5/2018 Border et al.
9,968,297 B2 5/2018 Connor
9,980,780 B2 5/2018 Lang
9,986,228 B2 5/2018 Woods
D824,523 S 7/2018 Paoli et al.
10,010,379 B1 7/2018 Gibby et al.
10,013,531 B2 7/2018 Richards et al.
10,015,243 B2 7/2018 Kazerani et al.
10,016,243 B2 7/2018 Esterberg
10,022,064 B2 7/2018 Kim et al.
10,022,065 B2 7/2018 Ben-Yishai et al.
10,022,104 B2 7/2018 Sell et al.
10,023,615 B2 7/2018 Bonny
10,026,015 B2 7/2018 Cavusoglu et al.
10,034,713 B2 7/2018 Yang et al.
10,042,167 B2 8/2018 Mcdowall et al.
10,046,165 B2 8/2018 Frewin et al.
10,055,838 B2 8/2018 Elenbaas et al.
10,066,816 B2 9/2018 Chang
10,067,359 B1 9/2018 Ushakov
10,073,515 B2 9/2018 Awdeh
10,080,616 B2 9/2018 Wilkinson et al.
10,082,680 B2 9/2018 Chung
10,085,709 B2 10/2018 Lavallee et al.
10,105,187 B2 10/2018 Corndorf et al.
10,107,483 B2 10/2018 Oren
10,108,833 B2 10/2018 Hong et al.
10,123,840 B2 11/2018 Dorman
10,130,378 B2 11/2018 Bryan
10,132,483 B1 11/2018 Feinbloom et al.
10,134,166 B2 11/2018 Benishti et al.
10,134,194 B2 11/2018 Kepner et al.
10,139,652 B2 11/2018 Windham
10,139,920 B2 11/2018 Isaacs et al.
10,142,496 B1 11/2018 Rao et al.
10,151,928 B2 12/2018 Ushakov
10,154,239 B2 12/2018 Casas
10,159,530 B2 12/2018 Lang
10,163,207 B2 12/2018 Merlet
10,166,079 B2 1/2019 Mclachlin et al.
10,175,507 B2 1/2019 Nakamura
10,175,753 B2 1/2019 Boesen
10,181,361 B2 1/2019 Dillavou et al.
10,186,055 B2 1/2019 Takahashi et al.
10,188,672 B2 1/2019 Wagner
10,194,131 B2 1/2019 Casas
10,194,990 B2 2/2019 Amanatullah et al.
10,194,993 B2 2/2019 Roger et al.
10,195,076 B2 2/2019 Fateh
10,197,803 B2 2/2019 Badiali et al.
10,197,816 B2 2/2019 Waisman et al.
10,207,315 B2 2/2019 Appleby et al.
10,212,517 B1 2/2019 Beltran et al.
10,230,719 B2 3/2019 Vaughn et al.
10,231,893 B2 3/2019 Lei et al.
10,235,606 B2 3/2019 Miao et al.
10,240,769 B1 3/2019 Braganca et al.
10,247,965 B2 4/2019 Ton
10,251,724 B2 4/2019 Mclachlin et al.
10,261,324 B2 4/2019 Chuang et al.
10,262,424 B2 4/2019 Ketcha et al.
10,274,731 B2 4/2019 Maimone
10,278,777 B1 5/2019 Lang
10,292,768 B2 5/2019 Lang
10,296,805 B2 5/2019 Yang et al.
10,319,154 B1 6/2019 Chakravarthula et al.
10,326,975 B2 6/2019 Casas
10,332,267 B2 6/2019 Rai et al.
10,339,719 B2 7/2019 Jagga et al.
10,352,543 B1 7/2019 Braganca et al.
10,357,146 B2 7/2019 Fiebel et al.
10,357,574 B2 7/2019 Hilderbrand et al.
10,366,489 B2 7/2019 Boettger et al.
10,368,947 B2 8/2019 Lang
10,368,948 B2 8/2019 Tripathi
10,382,748 B2 8/2019 Benishti et al.
10,383,654 B2 8/2019 Yilmaz et al.
10,386,645 B2 8/2019 Abou Shousha
10,388,076 B2 8/2019 Bar-Zeev et al.
10,398,514 B2 9/2019 Ryan et al.
10,401,657 B2 9/2019 Jiang et al.
10,405,825 B2 9/2019 Rai et al.
10,405,927 B1 9/2019 Lang
10,413,752 B2 9/2019 Berlinger et al.
10,419,655 B2 9/2019 Sivan
10,420,626 B2 9/2019 Tokuda et al.
10,420,813 B2 9/2019 Newell-Rogers et al.
10,424,115 B2 9/2019 Ellerbrock
D862,469 S 10/2019 Sadot et al.
10,426,554 B2 10/2019 Siewerdsen et al.
10,429,675 B2 10/2019 Greget
10,431,008 B2 10/2019 Djajadiningrat et al.
10,433,814 B2 10/2019 Razzaque et al.
10,434,335 B2 10/2019 Takahashi et al.
10,441,236 B2 10/2019 Bar-Tal et al.
10,444,514 B2 10/2019 Abou Shousha et al.
10,447,947 B2 10/2019 Liu
10,448,003 B2 10/2019 Grafenberg
10,449,040 B2 10/2019 Lashinski et al.
10,453,187 B2 10/2019 Peterson et al.
10,463,434 B2 11/2019 Siegler et al.
10,465,892 B1 11/2019 Feinbloom et al.
10,466,487 B2 11/2019 Blum et al.
10,470,732 B2 11/2019 Baumgart et al.
10,473,314 B1 11/2019 Braganca et al.
10,485,989 B2 11/2019 Jordan et al.
10,488,663 B2 11/2019 Choi
D869,772 S 12/2019 Gand
D870,977 S 12/2019 Berggren et al.
10,492,755 B2 12/2019 Lin et al.
10,499,997 B2 12/2019 Weinstein et al.
10,502,363 B2 12/2019 Edwards et al.
10,504,231 B2 12/2019 Fiala
10,507,066 B2 12/2019 Dimaio et al.
10,511,822 B2 12/2019 Casas
10,517,544 B2 12/2019 Taguchi et al.
10,537,395 B2 1/2020 Perez
10,540,780 B1 1/2020 Cousins et al.
10,543,485 B2 1/2020 Ismagilov et al.
10,546,423 B2 1/2020 Jones et al.
10,548,557 B2 2/2020 Lim et al.
10,555,775 B2 2/2020 Hoffman et al.
10,568,535 B2 2/2020 Roberts et al.
10,571,696 B2 2/2020 Urey et al.
10,571,716 B2 2/2020 Chapiro
10,573,086 B2 2/2020 Bar-Zeev et al.
10,573,087 B2 2/2020 Gallop et al.
10,577,630 B2 3/2020 Zhang et al.
10,586,400 B2 3/2020 Douglas
10,591,737 B2 3/2020 Yildiz et al.
10,592,748 B1 3/2020 Cousins et al.
10,594,998 B1 3/2020 Casas
10,595,716 B2 3/2020 Nazareth et al.
10,601,950 B2 3/2020 Devam et al.
10,602,114 B2 3/2020 Casas
10,603,113 B2 3/2020 Lang
10,603,133 B2 3/2020 Wang et al.
10,606,085 B2 3/2020 Toyama
10,610,172 B2 4/2020 Hummel et al.
10,610,179 B2 4/2020 Altmann
10,613,352 B2 4/2020 Knoll
10,617,566 B2 4/2020 Esmonde
10,620,460 B2 4/2020 Carabin
10,621,738 B2 4/2020 Miao et al.
10,625,099 B2 4/2020 Takahashi et al.
10,626,473 B2 4/2020 Mariani et al.

(56) References Cited

U.S. PATENT DOCUMENTS 10,631,905 B2 4/2020 Asfora et al.
10,631,907 B2 4/2020 Zucker et al.
10,634,331 B1 4/2020 Feinbloom et al.
10,634,921 B2 4/2020 Blum et al.
10,638,080 B2 4/2020 Ovchinnikov et al.
10,646,285 B2 5/2020 Siemionow et al.
10,650,513 B2 5/2020 Penney et al.
10,650,594 B2 5/2020 Jones et al.
10,652,525 B2 5/2020 Woods
10,653,495 B2 5/2020 Gregerson et al.
10,660,715 B2 5/2020 Dozeman
10,663,738 B2 5/2020 Carlvik et al.
10,665,033 B2 5/2020 Bar-Zeev et al.
10,670,937 B2 6/2020 Alton et al.
10,672,145 B2 6/2020 Albiol et al.
10,682,112 B2 6/2020 Pizaine et al.
10,682,767 B2 6/2020 Grafenberg et al.
10,687,901 B2 6/2020 Monroe
10,691,397 B1 6/2020 Clements
10,702,713 B2 7/2020 Mori et al.
10,706,540 B2 7/2020 Merlet
10,709,398 B2 7/2020 Schweizer
10,713,801 B2 7/2020 Jordan et al.
10,716,643 B2 7/2020 Justin et al.
10,722,733 B2 7/2020 Takahashi
10,725,535 B2 7/2020 Yu
10,731,832 B2 8/2020 Koo
10,732,721 B1 8/2020 Clements
10,742,949 B2 8/2020 Casas
10,743,939 B1 8/2020 Lang
10,743,943 B2 8/2020 Razeto et al.
10,747,315 B2 8/2020 Tungare et al.
10,748,319 B1 8/2020 Tao et al.
10,758,315 B2 9/2020 Johnson et al.
10,777,094 B1 9/2020 Rao et al.
10,777,315 B2 9/2020 Zehavi et al.
10,781,482 B2 9/2020 Gubatayao et al.
10,792,110 B2 10/2020 Leung et al.
10,799,145 B2 10/2020 West et al.
10,799,296 B2 10/2020 Lang
10,799,298 B2 10/2020 Crawford et al.
10,799,316 B2 10/2020 Sela et al.
10,810,799 B2 10/2020 Tepper et al.
10,818,019 B2 10/2020 Piat et al.
10,818,101 B2 10/2020 Gallop et al.
10,818,199 B2 10/2020 Buras et al.
10,825,563 B2 11/2020 Gibby et al.
10,827,164 B2 11/2020 Perreault et al.
10,831,943 B2 11/2020 Santarone et al.
10,835,296 B2 11/2020 Elimelech et al.
10,838,206 B2 11/2020 Fortin-Deschnes et al.
10,839,629 B2 11/2020 Jones et al.
10,839,956 B2 11/2020 Beydoun et al.
10,841,556 B2 11/2020 Casas
10,842,002 B2 11/2020 Chang
10,842,461 B2 11/2020 Johnson et al.
10,849,691 B2 12/2020 Zucker et al.
10,849,693 B2 12/2020 Lang
10,849,710 B2 12/2020 Liu
10,861,236 B2 12/2020 Geri et al.
10,865,220 B2 12/2020 Ebetino et al.
10,869,517 B1 12/2020 Halpern
10,869,727 B2 12/2020 Yanof et al.
10,872,472 B2 12/2020 Watola et al.
10,877,262 B1 12/2020 Luxembourg
10,877,296 B2 12/2020 Lindsey et al.
10,878,639 B2 12/2020 Douglas et al.
10,893,260 B2 1/2021 Trail et al.
10,895,742 B2 1/2021 Schneider et al.
10,895,743 B2 1/2021 Dausmann
10,895,906 B2 1/2021 West et al.
10,898,151 B2 1/2021 Harding et al.
10,908,420 B2 2/2021 Lee et al.
10,921,595 B2 2/2021 Rakshit et al.
10,921,613 B2 2/2021 Gupta et al.
10,928,321 B2 2/2021 Rawle
10,928,638 B2 2/2021 Ninan et al.
10,929,670 B1 2/2021 Troy et al.
10,935,815 B1 3/2021 Cesar
10,935,816 B2 3/2021 Ban et al.
10,936,537 B2 3/2021 Huston
10,939,973 B2 3/2021 Dimaio et al.
10,939,977 B2 3/2021 Messinger et al.
10,941,933 B2 3/2021 Ferguson
10,946,108 B2 3/2021 Zhang et al.
10,950,338 B2 3/2021 Douglas
10,951,872 B2 3/2021 Casas
10,964,095 B1 3/2021 Douglas
10,964,124 B1 3/2021 Douglas
10,966,768 B2 4/2021 Poulos
10,969,587 B2 4/2021 Mcdowall et al.
10,993,754 B2 5/2021 Kuntz et al.
11,000,335 B2 5/2021 Dorman
11,002,994 B2 5/2021 Jiang et al.
11,006,093 B1 5/2021 Hegyi
11,013,550 B2 5/2021 Rioux et al.
11,013,560 B2 5/2021 Lang
11,013,562 B2 5/2021 Marti et al.
11,013,573 B2 5/2021 Chang
11,013,900 B2 5/2021 Malek et al.
11,016,302 B2 5/2021 Freeman et al.
11,019,988 B2 6/2021 Fiebel et al.
11,027,027 B2 6/2021 Manning et al.
11,029,147 B2 6/2021 Abovitz et al.
11,030,809 B2 6/2021 Wang
11,041,173 B2 6/2021 Zhang et al.
11,045,663 B2 6/2021 Mori et al.
11,049,293 B2 6/2021 Chae et al.
11,049,476 B2 6/2021 Fuchs et al.
11,050,990 B2 6/2021 Casas
11,057,505 B2 7/2021 Dharmatilleke
11,058,390 B1 7/2021 Douglas
11,061,257 B1 7/2021 Hakim
11,064,904 B2 7/2021 Kay et al.
11,065,062 B2 7/2021 Frushour et al.
11,067,387 B2 7/2021 Marell et al.
11,071,497 B2 7/2021 Hallack et al.
11,079,596 B2 8/2021 Hua et al.
11,087,039 B2 8/2021 Duff et al.
11,090,019 B2 8/2021 Siemionow et al.
11,097,129 B2 8/2021 Sakata et al.
11,099,376 B1 8/2021 Steier et al.
11,103,320 B2 8/2021 Leboeuf et al.
D930,162 S 9/2021 Cremer et al.
11,109,762 B1 9/2021 Steier et al.
11,112,611 B1 9/2021 Kessler et al.
11,122,164 B2 9/2021 Gigante
11,123,604 B2 9/2021 Fung
11,129,562 B2 9/2021 Roberts et al.
11,132,055 B2 9/2021 Jones et al.
11,135,015 B2 10/2021 Crawford et al.
11,135,016 B2 10/2021 Frielinghaus et al.
11,137,610 B1 10/2021 Kessler et al.
11,141,221 B2 10/2021 Hobeika et al.
11,153,549 B2 10/2021 Casas
11,153,555 B1 10/2021 Healy et al.
11,163,176 B2 11/2021 Karafin et al.
11,164,324 B2 11/2021 Liu et al.
11,166,006 B2 11/2021 Hegyi
11,169,380 B2 11/2021 Manly et al.
11,172,990 B2 11/2021 Lang
11,179,136 B2 11/2021 Kohli et al.
11,180,557 B2 11/2021 Noelle
11,181,747 B1 11/2021 Kessler et al.
11,185,891 B2 11/2021 Cousins et al.
11,187,907 B2 11/2021 Osterman et al.
11,202,682 B2 12/2021 Staunton et al.
11,207,150 B2 12/2021 Healy et al.
11,217,028 B2 1/2022 Jones et al.
11,224,483 B2 1/2022 Steinberg et al.
11,224,763 B2 1/2022 Takahashi et al.
11,227,417 B2 1/2022 Berlinger et al.
11,231,787 B2 1/2022 Isaacs et al.
11,243,404 B2 2/2022 Mcdowall et al.

(56) References Cited

U.S. PATENT DOCUMENTS 11,244,508 B2 2/2022 Kazanzides et al.
11,253,216 B2 2/2022 Crawford et al.
11,253,323 B2 2/2022 Hughes et al.
11,257,190 B2 2/2022 Mao et al.
11,257,241 B2 2/2022 Tao
11,263,772 B2 3/2022 Siemionow et al.
11,269,401 B2 3/2022 West et al.
11,272,151 B2 3/2022 Casas
11,278,359 B2 3/2022 Siemionow et al.
11,278,413 B1 3/2022 Lang
11,280,480 B2 3/2022 Wilt et al.
11,284,846 B2 3/2022 Graumann et al.
11,291,521 B2 4/2022 Im
11,294,167 B2 4/2022 Ishimoda
11,297,285 B2 4/2022 Pierce
11,300,252 B2 4/2022 Nguyen
11,300,790 B2 4/2022 Cheng et al.
11,304,621 B2 4/2022 Merschon et al.
11,304,759 B2 4/2022 Kovtun et al.
11,307,402 B2 4/2022 Steier et al.
11,308,663 B2 4/2022 Alhrishy et al.
11,311,341 B2 4/2022 Lang
11,317,973 B2 5/2022 Calloway et al.
11,337,763 B2 5/2022 Choi
11,348,257 B2 5/2022 Lang
11,350,072 B1 5/2022 Quiles Casas
11,350,965 B2 6/2022 Yilmaz et al.
11,351,006 B2 6/2022 Aferzon et al.
11,354,813 B2 6/2022 Piat et al.
11,360,315 B2 6/2022 Tu et al.
11,373,342 B2 6/2022 Stafford et al.
11,382,699 B2 7/2022 Wassall et al.
11,382,700 B2 7/2022 Calloway et al.
11,382,712 B2 7/2022 Elimelech et al.
11,382,713 B2 7/2022 Healy et al.
11,389,252 B2 7/2022 Gera et al.
11,393,229 B2 7/2022 Zhou et al.
11,399,895 B2 8/2022 Soper et al.
11,402,524 B2 8/2022 Song et al.
11,406,338 B2 8/2022 Tolkowsky
11,412,202 B2 8/2022 Hegyi
11,423,554 B2 8/2022 Borsdorf et al.
11,430,203 B2 8/2022 Navab et al.
11,432,828 B1 9/2022 Lang
11,432,931 B2 9/2022 Lang
11,443,428 B2 9/2022 Petersen et al.
11,443,431 B2 9/2022 Flossmann et al.
11,452,568 B2 9/2022 Lang
11,452,570 B2 9/2022 Tolkowsky
11,460,915 B2 10/2022 Frielinghaus et al.
11,461,936 B2 10/2022 Freeman et al.
11,461,983 B2 10/2022 Jones et al.
11,464,580 B2 10/2022 Kemp et al.
11,464,581 B2 10/2022 Calloway
11,475,625 B1 10/2022 Douglas
11,478,214 B2 10/2022 Siewerdsen et al.
11,483,532 B2 10/2022 Quiles Casas
11,488,021 B2 11/2022 Sun et al.
11,490,986 B2 11/2022 Ben-Yishai
11,510,750 B2 11/2022 Dulin et al.
11,513,358 B2 11/2022 Mcdowall et al.
11,527,002 B2 12/2022 Govari
11,528,393 B2 12/2022 Garofolo et al.
11,544,031 B2 1/2023 Harviainen
11,573,420 B2 2/2023 Sarma et al.
11,589,927 B2 2/2023 Oezbek et al.
11,627,924 B2 4/2023 Alexandroni et al.
11,644,675 B2 5/2023 Manly et al.
11,648,016 B2 5/2023 Hathaway et al.
11,651,499 B2 5/2023 Wang et al.
11,657,518 B2 5/2023 Ketcha et al.
11,666,458 B2 6/2023 Kim et al.
11,669,984 B2 6/2023 Siewerdsen et al.
11,686,947 B2 6/2023 Loyola et al.
11,699,236 B2 7/2023 Avital et al.
11,712,582 B2 8/2023 Miyazaki et al.
11,715,210 B2 8/2023 Haslam et al.
11,719,941 B2 8/2023 Russell
11,730,389 B2 8/2023 Farshad et al.
11,733,516 B2 8/2023 Edwin et al.
11,734,901 B2 8/2023 Jones et al.
11,744,657 B2 9/2023 Leboeuf et al.
11,750,794 B2 9/2023 Benishti et al.
11,766,296 B2 9/2023 Wolf et al.
11,798,178 B2 10/2023 Merlet
11,801,097 B2 10/2023 Crawford et al.
11,801,115 B2 10/2023 Elimelech et al.
11,808,943 B2 11/2023 Robaina et al.
11,815,683 B2 11/2023 Sears et al.
11,826,111 B2 11/2023 Mahfouz
11,832,886 B2 12/2023 Dorman
11,838,493 B2 12/2023 Healy et al.
11,839,433 B2 12/2023 Schaewe et al.
11,839,501 B2 12/2023 Takahashi et al.
11,864,934 B2 1/2024 Junio et al.
11,885,752 B2 1/2024 St-Aubin et al.
11,892,647 B2 2/2024 Hung et al.
11,896,445 B2 2/2024 Gera et al.
11,900,620 B2 2/2024 Lalys et al.
11,914,155 B2 2/2024 Zhu et al.
11,918,310 B1 3/2024 Roh et al.
11,922,631 B2 3/2024 Haslam et al.
11,941,814 B2 3/2024 Crawford et al.
11,944,508 B1 4/2024 Cowin et al.
11,948,265 B2 4/2024 Gibby et al.
11,950,968 B2 4/2024 Wiggermann
11,957,420 B2 4/2024 Lang
11,961,193 B2 4/2024 Pelzl et al.
11,963,723 B2 4/2024 Vilsmeier et al.
11,972,582 B2 4/2024 Yan et al.
11,974,819 B2 5/2024 Finley et al.
11,974,887 B2 5/2024 Elimelech et al.
11,977,232 B2 5/2024 Wu et al.
11,980,429 B2 5/2024 Wolf et al.
11,980,506 B2 5/2024 Wolf et al.
11,980,507 B2 5/2024 Elimelech et al.
11,980,508 B2 5/2024 Elimelech et al.
11,983,824 B2 5/2024 Avisar et al.
12,002,171 B2 6/2024 Jones et al.
12,010,285 B2 6/2024 Quiles Casas
12,014,497 B2 6/2024 Hong et al.
12,019,314 B1 6/2024 Steines et al.
12,033,322 B2 7/2024 Laaksonen et al.
12,044,856 B2 7/2024 Gera et al.
12,044,858 B2 7/2024 Gera et al.
12,056,830 B2 8/2024 Cvetko et al.
12,059,281 B2 8/2024 Weingarten et al.
12,063,338 B2 8/2024 Quiles Casas
12,063,345 B2 8/2024 Benishti et al.
12,069,233 B2 8/2024 Benishti et al.
12,076,158 B2 9/2024 Geiger et al.
12,076,196 B2 9/2024 Elimelech et al.
12,079,385 B2 9/2024 Ben-Yishai et al.
2002/0082498 A1 6/2002 Wendt et al.
2003/0059097 A1 3/2003 Abovitz et al.
2003/0117393 A1 6/2003 Sauer et al.
2003/0130576 A1 7/2003 Seeley et al.
2003/0156144 A1 8/2003 Morita
2003/0210812 A1 11/2003 Khamene et al.
2003/0225329 A1 12/2003 Rossner et al.
2004/0019263 A1 1/2004 Jutras et al.
2004/0030237 A1 2/2004 Lee et al.
2004/0138556 A1 7/2004 Cosman
2004/0152955 A1 8/2004 Mcginley et al.
2004/0171930 A1 9/2004 Grimm et al.
2004/0238732 A1 12/2004 State et al.
2005/0017972 A1 1/2005 Poole et al.
2005/0024586 A1 2/2005 Teiwes et al.
2005/0119639 A1 6/2005 Mccombs et al.
2005/0154296 A1 7/2005 Lechner et al.
2005/0203367 A1 9/2005 Ahmed et al.
2005/0203380 A1 9/2005 Sauer et al.
2005/0215879 A1 9/2005 Chuanggui
2005/0267358 A1 12/2005 Tuma et al.

(56) References Cited

U.S. PATENT DOCUMENTS

2006/0072124 A1 4/2006 Smetak et al.
2006/0134198 A1 6/2006 Tawa et al.
2006/0147100 A1 7/2006 Fitzpatrick
2006/0176242 A1 8/2006 Jaramaz et al.
2007/0018975 A1 1/2007 Chuanggui et al.
2007/0058261 A1 3/2007 Sugihara et al.
2007/0100325 A1 5/2007 Jutras et al.
2007/0183041 A1 8/2007 Mccloy et al.
2007/0233371 A1 10/2007 Stoschek et al.
2007/0273610 A1 11/2007 Baillot
2008/0002809 A1 1/2008 Bodduluri
2008/0007645 A1 1/2008 McCutchen
2008/0035266 A1 2/2008 Danziger
2008/0085033 A1 4/2008 Haven et al.
2008/0159612 A1 7/2008 Fu et al.
2008/0183065 A1 7/2008 Goldbach
2008/0221625 A1 9/2008 Hufner et al.
2008/0253527 A1 10/2008 Boyden et al.
2008/0262812 A1 10/2008 Arata et al.
2008/0287728 A1 11/2008 Mostafavi et al.
2009/0005961 A1 1/2009 Grabowski et al.
2009/0018437 A1 1/2009 Cooke
2009/0024127 A1 1/2009 Lechner et al.
2009/0036902 A1 2/2009 Dimaio et al.
2009/0062869 A1 3/2009 Claverie et al.
2009/0099445 A1 4/2009 Burger
2009/0123452 A1 5/2009 Madison
2009/0227847 A1 9/2009 Tepper et al.
2009/0285366 A1 11/2009 Essenreiter et al.
2009/0300540 A1 12/2009 Russell
2010/0076305 A1 3/2010 Maier-Hein et al.
2010/0094308 A1 4/2010 Tatsumi et al.
2010/0106010 A1 4/2010 Rubner et al.
2010/0114110 A1 5/2010 Taft et al.
2010/0138939 A1 6/2010 Bentzon et al.
2010/0149073 A1 6/2010 Chaum et al.
2010/0172567 A1 7/2010 Prokoski
2010/0210939 A1 8/2010 Hartmann et al.
2010/0266220 A1 10/2010 Zagorchev et al.
2010/0274124 A1 10/2010 Jascob et al.
2011/0004259 A1 1/2011 Stallings et al.
2011/0098553 A1 4/2011 Robbins et al.
2011/0105895 A1 5/2011 Kornblau et al.
2011/0216060 A1 9/2011 Weising et al.
2011/0245625 A1 10/2011 Trovato et al.
2011/0248064 A1 10/2011 Marczyk
2011/0254922 A1 10/2011 Schaerer et al.
2011/0306873 A1 12/2011 Shenai et al.
2012/0014608 A1 1/2012 Watanabe
2012/0068913 A1 3/2012 Bar-Zeev et al.
2012/0078236 A1 3/2012 Schoepp
2012/0109151 A1 5/2012 Maier-Hein et al.
2012/0143050 A1 6/2012 Heigl
2012/0155064 A1 6/2012 Waters
2012/0162452 A1 6/2012 Liu
2012/0182605 A1 7/2012 Hall et al.
2012/0201421 A1 8/2012 Hartmann et al.
2012/0216411 A1 8/2012 Wevers et al.
2012/0224260 A1 9/2012 Healy et al.
2012/0238609 A1 9/2012 Srivastava et al.
2012/0289777 A1 11/2012 Chopra et al.
2012/0306850 A1 12/2012 Balan et al.
2012/0320100 A1 12/2012 Machida et al.
2013/0002928 A1 1/2013 Imai
2013/0009853 A1 1/2013 Hesselink et al.
2013/0038632 A1 2/2013 Dillavou et al.
2013/0050258 A1 2/2013 Liu et al.
2013/0050833 A1 2/2013 Lewis et al.
2013/0057581 A1 3/2013 Meier
2013/0079829 A1 3/2013 Globerman et al.
2013/0083009 A1 4/2013 Geisner et al.
2013/0106833 A1 5/2013 Fun
2013/0135734 A1 5/2013 Shafer et al.
2013/0135738 A1 5/2013 Shafer et al.
2013/0190602 A1 7/2013 Liao et al.
2013/0195338 A1 8/2013 Xu et al.
2013/0209953 A1 8/2013 Arlinsky et al.
2013/0212453 A1 8/2013 Gudai et al.
2013/0234914 A1 9/2013 Fujimaki
2013/0234935 A1 9/2013 Griffith
2013/0237811 A1 9/2013 Mihailescu et al.
2013/0245461 A1 9/2013 Maier-Hein et al.
2013/0249787 A1 9/2013 Morimoto
2013/0249945 A1 9/2013 Kobayashi
2013/0265623 A1 10/2013 Sugiyama et al.
2013/0267838 A1 10/2013 Fronk et al.
2013/0278631 A1 10/2013 Border et al.
2013/0278635 A1 10/2013 Maggiore
2013/0300637 A1 11/2013 Smits et al.
2013/0300760 A1 11/2013 Sugano et al.
2013/0342571 A1 12/2013 Kinnebrew et al.
2013/0345718 A1 12/2013 Crawford et al.
2014/0031668 A1 1/2014 Mobasser et al.
2014/0049629 A1 2/2014 Siewerdsen et al.
2014/0088402 A1 3/2014 Xu
2014/0088990 A1 3/2014 Nawana et al.
2014/0104505 A1 4/2014 Koenig
2014/0105912 A1 4/2014 Noelle
2014/0114173 A1 4/2014 Bar-Tal et al.
2014/0142426 A1 5/2014 Razzaque et al.
2014/0168261 A1 6/2014 Margolis et al.
2014/0176661 A1 6/2014 Smurro et al.
2014/0177023 A1 6/2014 Gao et al.
2014/0189508 A1 7/2014 Granchi et al.
2014/0198129 A1 7/2014 Liu et al.
2014/0218291 A1 8/2014 Kirk
2014/0240484 A1 8/2014 Kodama et al.
2014/0243614 A1 8/2014 Rothberg et al.
2014/0256429 A1 9/2014 Kobayashi et al.
2014/0266983 A1 9/2014 Christensen
2014/0268356 A1 9/2014 Bolas et al.
2014/0270505 A1 9/2014 Mccarthy
2014/0275760 A1 9/2014 Lee et al.
2014/0285404 A1 9/2014 Takano et al.
2014/0285429 A1 9/2014 Simmons
2014/0300632 A1 10/2014 Laor
2014/0300967 A1 10/2014 Tilleman et al.
2014/0301624 A1 10/2014 Barckow et al.
2014/0303491 A1 10/2014 Shekhar et al.
2014/0320399 A1 10/2014 Kim et al.
2014/0333899 A1 11/2014 Smithwick
2014/0336461 A1 11/2014 Reiter et al.
2014/0340286 A1 11/2014 Machida et al.
2014/0361956 A1 12/2014 Mikhailov et al.
2014/0371728 A1 12/2014 Vaughn
2015/0005772 A1 1/2015 Anglin et al.
2015/0018672 A1 1/2015 Blumhofer et al.
2015/0031985 A1* 1/2015 Reddy .................... A61B 34/20
600/424
2015/0043798 A1 2/2015 Carrell et al.
2015/0070347 A1 3/2015 Hofmann et al.
2015/0084990 A1 3/2015 Laor
2015/0150641 A1 6/2015 Daon et al.
2015/0182293 A1 7/2015 Yang et al.
2015/0192776 A1 7/2015 Lee et al.
2015/0209119 A1 7/2015 Theodore et al.
2015/0230873 A1 8/2015 Kubiak et al.
2015/0230893 A1 8/2015 Huwais
2015/0261922 A1 9/2015 Nawana et al.
2015/0277123 A1 10/2015 Chaum et al.
2015/0282735 A1 10/2015 Rossner
2015/0287188 A1 10/2015 Gazit et al.
2015/0287236 A1 10/2015 Winne et al.
2015/0297314 A1 10/2015 Fowler et al.
2015/0305828 A1 10/2015 Park et al.
2015/0310668 A1 10/2015 Ellerbrock
2015/0338652 A1 11/2015 Lim et al.
2015/0338653 A1 11/2015 Subramaniam et al.
2015/0350517 A1 12/2015 Duret et al.
2015/0351863 A1 12/2015 Plassky et al.
2015/0363978 A1 12/2015 Maimone et al.
2015/0366620 A1 12/2015 Cameron et al.
2016/0015878 A1 1/2016 Graham et al.
2016/0022287 A1 1/2016 Nehls

(56) References Cited

U.S. PATENT DOCUMENTS

2016/0030131 A1 2/2016 Yang et al.
2016/0054571 A1 2/2016 Tazbaz et al.
2016/0086380 A1 3/2016 Vayser et al.
2016/0103318 A1 4/2016 Du et al.
2016/0125603 A1 5/2016 Tanji
2016/0133051 A1 5/2016 Aonuma et al.
2016/0143699 A1 5/2016 Tanji
2016/0153004 A1 6/2016 Zhang et al.
2016/0163045 A1 6/2016 Penney et al.
2016/0175064 A1 6/2016 Steinle et al.
2016/0178910 A1 6/2016 Giudicelli et al.
2016/0191887 A1 6/2016 Casas
2016/0223822 A1 8/2016 Harrison et al.
2016/0228033 A1 8/2016 Rossner
2016/0246059 A1 8/2016 Halpin et al.
2016/0249989 A1 9/2016 Devam et al.
2016/0256223 A1 9/2016 Haimerl et al.
2016/0275684 A1 9/2016 Elenbaas et al.
2016/0297315 A1 10/2016 Gonzalez et al.
2016/0302870 A1 10/2016 Wilkinson et al.
2016/0324580 A1 11/2016 Esterberg
2016/0324583 A1 11/2016 Kheradpir et al.
2016/0339337 A1 11/2016 Ellsworth et al.
2017/0014119 A1 1/2017 Capote et al.
2017/0024634 A1 1/2017 Miao et al.
2017/0027650 A1 2/2017 Merck et al.
2017/0031163 A1 2/2017 Gao et al.
2017/0031179 A1 2/2017 Guillot et al.
2017/0045742 A1 2/2017 Greenhalgh et al.
2017/0065364 A1 3/2017 Schuh et al.
2017/0068119 A1 3/2017 Antaki et al.
2017/0076501 A1 3/2017 Jagga et al.
2017/0086941 A1 3/2017 Marti et al.
2017/0112586 A1 4/2017 Dhupar
2017/0164919 A1 6/2017 Lavallee et al.
2017/0164920 A1 6/2017 Lavallee et al.
2017/0178375 A1 6/2017 Benishti et al.
2017/0220224 A1 8/2017 Kodali et al.
2017/0239015 A1 8/2017 Sela et al.
2017/0245944 A1 8/2017 Crawford et al.
2017/0251900 A1 9/2017 Hansen et al.
2017/0252109 A1 9/2017 Yang et al.
2017/0258526 A1 9/2017 Lang
2017/0281283 A1 10/2017 Siegler et al.
2017/0312032 A1 11/2017 Amanatullah et al.
2017/0322950 A1 11/2017 Han et al.
2017/0348055 A1 12/2017 Salcedo et al.
2017/0348061 A1 12/2017 Joshi et al.
2017/0366773 A1 12/2017 Kiraly et al.
2017/0367766 A1 12/2017 Mahfouz
2017/0367771 A1 12/2017 Tako et al.
2017/0372477 A1 12/2017 Penney et al.
2018/0003981 A1 1/2018 Urey
2018/0018791 A1 1/2018 Guoyi
2018/0021597 A1 1/2018 Berlinger et al.
2018/0028266 A1 2/2018 Barnes et al.
2018/0036884 A1 2/2018 Chen et al.
2018/0049622 A1 2/2018 Ryan et al.
2018/0055579 A1 3/2018 Daon et al.
2018/0071029 A1 3/2018 Srimohanarajah et al.
2018/0078316 A1 3/2018 Schaewe et al.
2018/0082480 A1 3/2018 White et al.
2018/0092667 A1 4/2018 Heigl et al.
2018/0092698 A1 4/2018 Chopra et al.
2018/0092699 A1 4/2018 Finley
2018/0116732 A1 5/2018 Lin et al.
2018/0116741 A1 5/2018 Garcia et al.
2018/0117150 A1 5/2018 O'Dwyer et al.
2018/0120106 A1 5/2018 Sato
2018/0133871 A1 5/2018 Farmer
2018/0153626 A1 6/2018 Yang et al.
2018/0182150 A1 6/2018 Benishti et al.
2018/0185100 A1 7/2018 Weinstein et al.
2018/0185113 A1 7/2018 Gregerson et al.
2018/0193097 A1 7/2018 Mclachlin et al.
2018/0200002 A1 7/2018 Kostrzewski et al.
2018/0235714 A1* 8/2018 Kuo .................... A61B 34/20
2018/0247128 A1 8/2018 Alvi et al.
2018/0262743 A1 9/2018 Casas
2018/0303558 A1 10/2018 Monroe
2018/0311011 A1 11/2018 Van et al.
2018/0317803 A1 11/2018 Ben-Yishai et al.
2018/0318035 A1 11/2018 Mclachlin et al.
2018/0368898 A1 12/2018 Divincenzo et al.
2019/0000372 A1* 1/2019 Gullotti ................ A61B 5/4566
2019/0000564 A1 1/2019 Navab et al.
2019/0015163 A1 1/2019 Abhari et al.
2019/0018235 A1 1/2019 Ouderkirk et al.
2019/0038362 A1 2/2019 Nash et al.
2019/0038365 A1 2/2019 Soper et al.
2019/0043238 A1 2/2019 Benishti et al.
2019/0043392 A1 2/2019 Abele
2019/0046272 A1 2/2019 Zoabi et al.
2019/0046276 A1 2/2019 Inglese et al.
2019/0053851 A1 2/2019 Siemionow et al.
2019/0069971 A1 3/2019 Tripathi et al.
2019/0080515 A1 3/2019 Geri et al.
2019/0105116 A1 4/2019 Johnson et al.
2019/0130792 A1 5/2019 Rios et al.
2019/0142519 A1 5/2019 Siemionow et al.
2019/0144443 A1 5/2019 Jackson et al.
2019/0175228 A1 6/2019 Elimelech et al.
2019/0192230 A1 6/2019 Siemionow et al.
2019/0200894 A1 7/2019 Jung et al.
2019/0201106 A1 7/2019 Siemionow et al.
2019/0205606 A1 7/2019 Zhou et al.
2019/0216537 A1 7/2019 Eltorai et al.
2019/0251692 A1 8/2019 Schmidt-Richberg et al.
2019/0251694 A1 8/2019 Han et al.
2019/0254753 A1 8/2019 Johnson et al.
2019/0273916 A1 9/2019 Benishti et al.
2019/0310481 A1 10/2019 Blum et al.
2019/0333480 A1 10/2019 Lang
2019/0369660 A1 12/2019 Wen et al.
2019/0369717 A1 12/2019 Frielinghaus et al.
2019/0378276 A1 12/2019 Flossmann et al.
2019/0387351 A1 12/2019 Lyren et al.
2020/0015895 A1 1/2020 Frielinghaus et al.
2020/0019364 A1 1/2020 Pond
2020/0020249 A1 1/2020 Jarc et al.
2020/0038112 A1 2/2020 Amanatullah et al.
2020/0043160 A1 2/2020 Mizukura et al.
2020/0078100 A1 3/2020 Weinstein et al.
2020/0085511 A1 3/2020 Oezbek et al.
2020/0088997 A1 3/2020 Lee et al.
2020/0100847 A1 4/2020 Siegler et al.
2020/0117025 A1 4/2020 Sauer
2020/0129058 A1 4/2020 Li et al.
2020/0129136 A1 4/2020 Harding et al.
2020/0129262 A1 4/2020 Verard et al.
2020/0129264 A1 4/2020 Oativia et al.
2020/0133029 A1 4/2020 Yonezawa
2020/0138518 A1 5/2020 Lang
2020/0138618 A1 5/2020 Roszkowiak et al.
2020/0143594 A1 5/2020 Lal et al.
2020/0146546 A1 5/2020 Chene et al.
2020/0151507 A1 5/2020 Siemionow et al.
2020/0156259 A1 5/2020 Ruiz et al.
2020/0159313 A1 5/2020 Gibby et al.
2020/0163723 A1 5/2020 Wolf et al.
2020/0163739 A1 5/2020 Messinger et al.
2020/0178916 A1 6/2020 Lalys et al.
2020/0184638 A1 6/2020 Meglan et al.
2020/0186786 A1 6/2020 Gibby et al.
2020/0188028 A1 6/2020 Feiner et al.
2020/0188034 A1 6/2020 Lequette et al.
2020/0201082 A1 6/2020 Carabin
2020/0229877 A1 7/2020 Siemionow et al.
2020/0237256 A1 7/2020 Farshad et al.
2020/0237444 A1* 7/2020 Snyder .................. G06T 7/246
2020/0237459 A1 7/2020 Racheli et al.
2020/0237880 A1 7/2020 Kent et al.
2020/0242280 A1 7/2020 Pavloff et al.
2020/0246074 A1 8/2020 Lang

(56) References Cited

U.S. PATENT DOCUMENTS

2020/0246081 A1 8/2020 Johnson et al.
2020/0264451 A1 8/2020 Blum et al.
2020/0265273 A1 8/2020 Wei et al.
2020/0275988 A1 9/2020 Johnson et al.
2020/0281554 A1 9/2020 Trini et al.
2020/0286222 A1 9/2020 Essenreiter et al.
2020/0288075 A1 9/2020 Bonin et al.
2020/0294233 A1 9/2020 Merlet
2020/0297427 A1 9/2020 Cameron et al.
2020/0305980 A1 10/2020 Lang
2020/0315734 A1 10/2020 El Amm
2020/0321099 A1 10/2020 Holladay et al.
2020/0323460 A1 10/2020 Busza et al.
2020/0323609 A1 10/2020 Johnson et al.
2020/0327721 A1 10/2020 Siemionow et al.
2020/0330179 A1 10/2020 Ton
2020/0337780 A1 10/2020 Winkler et al.
2020/0341283 A1 10/2020 Mccracken et al.
2020/0352655 A1 11/2020 Freese
2020/0355927 A1 11/2020 Marcellin-Dibon et al.
2020/0360091 A1 11/2020 Murray et al.
2020/0375666 A1 12/2020 Stephen
2020/0377493 A1 12/2020 Heiser et al.
2020/0377956 A1 12/2020 Vogelstein et al.
2020/0388075 A1 12/2020 Kazanzides et al.
2020/0389425 A1 12/2020 Bhatia et al.
2020/0390502 A1 12/2020 Holthuizen et al.
2020/0390503 A1 12/2020 Casas et al.
2020/0402647 A1 12/2020 Domracheva et al.
2020/0409306 A1 12/2020 Gelman et al.
2020/0410687 A1 12/2020 Siemionow et al.
2020/0413031 A1 12/2020 Khani et al.
2021/0004956 A1 1/2021 Book et al.
2021/0009339 A1 1/2021 Morrison et al.
2021/0015560 A1 1/2021 Boddington et al.
2021/0015583 A1 1/2021 Avisar et al.
2021/0022599 A1 1/2021 Freeman et al.
2021/0022808 A1 1/2021 Lang
2021/0022811 A1 1/2021 Mahfouz
2021/0022828 A1 1/2021 Elimelech et al.
2021/0029804 A1 1/2021 Chang
2021/0030374 A1 2/2021 Takahashi et al.
2021/0030511 A1 2/2021 Wolf et al.
2021/0038339 A1 2/2021 Yu et al.
2021/0049825 A1 2/2021 Wheelwright et al.
2021/0052348 A1 2/2021 Stifter et al.
2021/0056687 A1 2/2021 Hibbard et al.
2021/0065911 A1 3/2021 Goel et al.
2021/0077195 A1 3/2021 Saeidi et al.
2021/0077210 A1 3/2021 Itkowitz et al.
2021/0080751 A1 3/2021 Lindsey et al.
2021/0090344 A1 3/2021 Geri et al.
2021/0093391 A1 4/2021 Poltaretskyi et al.
2021/0093392 A1 4/2021 Poltaretskyi et al.
2021/0093400 A1 4/2021 Quaid et al.
2021/0093417 A1 4/2021 Liu
2021/0104055 A1 4/2021 Ni et al.
2021/0107923 A1 4/2021 Jackson et al.
2021/0109349 A1 4/2021 Schneider et al.
2021/0109373 A1 4/2021 Loo et al.
2021/0110517 A1 4/2021 Flohr et al.
2021/0113269 A1 4/2021 Vilsmeier et al.
2021/0113293 A9 4/2021 Silva et al.
2021/0121238 A1 4/2021 Palushi et al.
2021/0137634 A1 5/2021 Lang
2021/0141887 A1 5/2021 Kim et al.
2021/0150702 A1 5/2021 Claessen et al.
2021/0157544 A1 5/2021 Denton
2021/0160472 A1 5/2021 Casas
2021/0161614 A1 6/2021 Elimelech et al.
2021/0162287 A1 6/2021 Xing et al.
2021/0165207 A1 6/2021 Peyman
2021/0169504 A1 6/2021 Brown
2021/0169578 A1 6/2021 Calloway et al.
2021/0169581 A1 6/2021 Calloway et al.
2021/0169605 A1 6/2021 Calloway et al.
2021/0186647 A1 6/2021 Elimelech et al.
2021/0192759 A1* 6/2021 Lang ...................... A61B 90/37
2021/0196404 A1 7/2021 Wang
2021/0211640 A1 7/2021 Bristol et al.
2021/0223577 A1 7/2021 Zhang et al.
2021/0225006 A1 7/2021 Grady et al.
2021/0227791 A1 7/2021 De et al.
2021/0231301 A1 7/2021 Hikmet et al.
2021/0235061 A1 7/2021 Hegyi
2021/0248822 A1 8/2021 Choi et al.
2021/0274281 A1 9/2021 Zhang et al.
2021/0278675 A1 9/2021 Klug et al.
2021/0282887 A1 9/2021 Wiggermann
2021/0290046 A1 9/2021 Nazareth et al.
2021/0290336 A1 9/2021 Wang
2021/0290394 A1 9/2021 Mahfouz
2021/0295108 A1 9/2021 Bar
2021/0295512 A1 9/2021 Knoplioch et al.
2021/0298795 A1 9/2021 Bowling et al.
2021/0298835 A1 9/2021 Wang
2021/0306599 A1 9/2021 Pierce
2021/0311322 A1 10/2021 Belanger et al.
2021/0314502 A1 10/2021 Liu
2021/0315636 A1 10/2021 Akbarian et al.
2021/0315662 A1 10/2021 Freeman et al.
2021/0325684 A1 10/2021 Ninan et al.
2021/0332447 A1 10/2021 Lubelski et al.
2021/0333561 A1 10/2021 Oh et al.
2021/0341739 A1 11/2021 Cakmakci et al.
2021/0341740 A1 11/2021 Cakmakci et al.
2021/0346115 A1 11/2021 Dulin et al.
2021/0349677 A1 11/2021 Baldev et al.
2021/0364802 A1 11/2021 Uchiyama et al.
2021/0369226 A1 12/2021 Siemionow et al.
2021/0371413 A1 12/2021 Thurston et al.
2021/0373333 A1 12/2021 Moon
2021/0373344 A1 12/2021 Loyola et al.
2021/0378757 A1 12/2021 Bay et al.
2021/0382310 A1 12/2021 Freeman et al.
2021/0386482 A1 12/2021 Gera et al.
2021/0389590 A1 12/2021 Freeman et al.
2021/0400247 A1 12/2021 Casas
2021/0401533 A1 12/2021 Im
2021/0402255 A1 12/2021 Fung
2021/0405369 A1 12/2021 King
2022/0003992 A1 1/2022 Ahn
2022/0007006 A1 1/2022 Healy et al.
2022/0008135 A1 1/2022 Frielinghaus et al.
2022/0038675 A1 2/2022 Hegyi
2022/0039873 A1 2/2022 Harris
2022/0051484 A1 2/2022 Jones et al.
2022/0054199 A1 2/2022 Sivaprakasam et al.
2022/0061921 A1 3/2022 Crawford et al.
2022/0071712 A1 3/2022 Wolf et al.
2022/0079675 A1 3/2022 Lang
2022/0087746 A1 3/2022 Lang
2022/0113810 A1 4/2022 Isaacs et al.
2022/0117669 A1 4/2022 Nikou et al.
2022/0121041 A1 4/2022 Hakim
2022/0133484 A1 5/2022 Lang
2022/0142730 A1 5/2022 Wolf et al.
2022/0155861 A1 5/2022 Myung et al.
2022/0159227 A1 5/2022 Quiles Casas
2022/0179209 A1 6/2022 Cherukuri
2022/0192776 A1 6/2022 Gibby et al.
2022/0193453 A1 6/2022 Miyazaki et al.
2022/0201274 A1 6/2022 Achilefu et al.
2022/0245400 A1 8/2022 Siemionow et al.
2022/0245821 A1 8/2022 Ouzounis
2022/0257206 A1 8/2022 Hartley et al.
2022/0269077 A1 8/2022 Adema et al.
2022/0270263 A1 8/2022 Junio
2022/0287676 A1 9/2022 Steines et al.
2022/0292786 A1 9/2022 Pelzl et al.
2022/0295033 A1 9/2022 Quiles Casas
2022/0296315 A1 9/2022 Sokhanvar et al.
2022/0304768 A1 9/2022 Elimelech et al.
2022/0351385 A1 11/2022 Finley et al.

(56) References Cited

U.S. PATENT DOCUMENTS

| | | | |
|---|---|---|---|
| 2022/0353487 | A1 | 11/2022 | Hegyi |
| 2022/0358759 | A1 | 11/2022 | Cork et al. |
| 2022/0361959 | A1* | 11/2022 | Weber .................... A61B 34/30 |
| 2022/0370152 | A1 | 11/2022 | Lavallee et al. |
| 2022/0387130 | A1 | 12/2022 | Spaas et al. |
| 2022/0392085 | A1 | 12/2022 | Finley et al. |
| 2022/0397750 | A1 | 12/2022 | Zhou et al. |
| 2022/0398752 | A1 | 12/2022 | Yoon et al. |
| 2022/0398755 | A1 | 12/2022 | Herrmann |
| 2022/0405935 | A1 | 12/2022 | Flossmann et al. |
| 2023/0004013 | A1 | 1/2023 | Mccracken et al. |
| 2023/0009793 | A1 | 1/2023 | Gera et al. |
| 2023/0025480 | A1 | 1/2023 | Kemp et al. |
| 2023/0027801 | A1 | 1/2023 | Qian et al. |
| 2023/0032731 | A1 | 2/2023 | Hrndler et al. |
| 2023/0034189 | A1 | 2/2023 | Gera et al. |
| 2023/0050636 | A1 | 2/2023 | Yanof et al. |
| 2023/0053120 | A1 | 2/2023 | Jamali et al. |
| 2023/0073041 | A1 | 3/2023 | Samadani et al. |
| 2023/0085387 | A1 | 3/2023 | Jones et al. |
| 2023/0087783 | A1 | 3/2023 | Dulin et al. |
| 2023/0100078 | A1 | 3/2023 | Toporek et al. |
| 2023/0123621 | A1 | 4/2023 | Joshi et al. |
| 2023/0126207 | A1 | 4/2023 | Wang |
| 2023/0129056 | A1 | 4/2023 | Hemingway et al. |
| 2023/0131515 | A1 | 4/2023 | Oezbek et al. |
| 2023/0149083 | A1 | 5/2023 | Lin et al. |
| 2023/0162493 | A1 | 5/2023 | Worrell et al. |
| 2023/0165640 | A1 | 6/2023 | Dulin et al. |
| 2023/0169659 | A1 | 6/2023 | Chen et al. |
| 2023/0196582 | A1 | 6/2023 | Grady et al. |
| 2023/0200917 | A1 | 6/2023 | Calloway et al. |
| 2023/0236426 | A1 | 7/2023 | Manly et al. |
| 2023/0236427 | A1 | 7/2023 | Jiannyuh |
| 2023/0260142 | A1 | 8/2023 | Chatterjee et al. |
| 2023/0290037 | A1 | 9/2023 | Tasse et al. |
| 2023/0295302 | A1 | 9/2023 | Bhagavatheeswaran et al. |
| 2023/0306590 | A1 | 9/2023 | Jazdzyk et al. |
| 2023/0316550 | A1 | 10/2023 | Hiasa |
| 2023/0326011 | A1 | 10/2023 | Cutforth et al. |
| 2023/0326027 | A1 | 10/2023 | Wahrenberg |
| 2023/0329799 | A1 | 10/2023 | Gera et al. |
| 2023/0329801 | A1 | 10/2023 | Elimelech et al. |
| 2023/0334664 | A1 | 10/2023 | Lu et al. |
| 2023/0335261 | A1 | 10/2023 | Reicher et al. |
| 2023/0359043 | A1 | 11/2023 | Russell |
| 2023/0363832 | A1 | 11/2023 | Mosadegh et al. |
| 2023/0371984 | A1 | 11/2023 | Leuthardt et al. |
| 2023/0372053 | A1 | 11/2023 | Elimelech et al. |
| 2023/0372054 | A1 | 11/2023 | Elimelech et al. |
| 2023/0377171 | A1 | 11/2023 | Hasler et al. |
| 2023/0377175 | A1 | 11/2023 | Seok |
| 2023/0379448 | A1 | 11/2023 | Benishti et al. |
| 2023/0379449 | A1 | 11/2023 | Benishti et al. |
| 2023/0386022 | A1 | 11/2023 | Tan et al. |
| 2023/0386067 | A1 | 11/2023 | De et al. |
| 2023/0386153 | A1 | 11/2023 | Rybnikov et al. |
| 2023/0394791 | A1 | 12/2023 | Wang et al. |
| 2023/0397349 | A1 | 12/2023 | Capelli et al. |
| 2023/0397957 | A1 | 12/2023 | Crawford et al. |
| 2023/0410445 | A1 | 12/2023 | Elimelech et al. |
| 2023/0419496 | A1 | 12/2023 | Wuelker et al. |
| 2023/0420114 | A1 | 12/2023 | Scholler et al. |
| 2024/0008935 | A1 | 1/2024 | Wolf et al. |
| 2024/0016549 | A1 | 1/2024 | Johnson et al. |
| 2024/0016572 | A1 | 1/2024 | Elimelech et al. |
| 2024/0020831 | A1 | 1/2024 | Johnson et al. |
| 2024/0020840 | A1 | 1/2024 | Johnson et al. |
| 2024/0020862 | A1 | 1/2024 | Johnson et al. |
| 2024/0022704 | A1 | 1/2024 | Benishti et al. |
| 2024/0023946 | A1 | 1/2024 | Wolf et al. |
| 2024/0041530 | A1 | 2/2024 | Lang |
| 2024/0041558 | A1 | 2/2024 | Siewerdsen et al. |
| 2024/0045491 | A1 | 2/2024 | Sourov |
| 2024/0058064 | A1 | 2/2024 | Weiser et al. |
| 2024/0062387 | A1 | 2/2024 | Frantz et al. |
| 2024/0103271 | A1 | 3/2024 | Zare Seisan |
| 2024/0103282 | A1 | 3/2024 | Law et al. |
| 2024/0111163 | A1 | 4/2024 | Law et al. |
| 2024/0122560 | A1 | 4/2024 | Junio et al. |
| 2024/0126087 | A1 | 4/2024 | Gera et al. |
| 2024/0127559 | A1 | 4/2024 | Rybnikov et al. |
| 2024/0127578 | A1 | 4/2024 | Hiasa |
| 2024/0129451 | A1 | 4/2024 | Healy et al. |
| 2024/0130826 | A1 | 4/2024 | Elimelech et al. |
| 2024/0134206 | A1 | 4/2024 | Gera et al. |
| 2024/0144497 | A1 | 5/2024 | Cvetko et al. |
| 2024/0156532 | A1 | 5/2024 | Weiman et al. |
| 2024/0177445 | A1 | 5/2024 | Galeotti et al. |
| 2024/0177458 | A1 | 5/2024 | Zhang et al. |
| 2024/0180634 | A1 | 6/2024 | Mikus |
| 2024/0184119 | A1 | 6/2024 | Lee et al. |
| 2024/0185509 | A1 | 6/2024 | Kovler et al. |
| 2024/0202926 | A1 | 6/2024 | Crawford et al. |
| 2024/0202927 | A1 | 6/2024 | Haslam et al. |
| 2024/0212111 | A1 | 6/2024 | Genghi et al. |
| 2024/0233131 | A1 | 7/2024 | Westerhoff et al. |
| 2024/0245463 | A1 | 7/2024 | Vilsmeier et al. |
| 2024/0245474 | A1 | 7/2024 | Weiman et al. |
| 2024/0248530 | A1 | 7/2024 | Gibby et al. |
| 2024/0252252 | A1 | 8/2024 | Lang |
| 2024/0261036 | A1 | 8/2024 | Finley et al. |
| 2024/0261058 | A1 | 8/2024 | Gera et al. |
| 2024/0265645 | A1 | 8/2024 | Papar |
| 2024/0266033 | A1 | 8/2024 | Freeman et al. |
| 2024/0268922 | A1 | 8/2024 | Calloway et al. |
| 2024/0273740 | A1 | 8/2024 | Gibby et al. |
| 2024/0281979 | A1 | 8/2024 | Schrempf et al. |
| 2024/0296527 | A1 | 9/2024 | Nett et al. |
| 2024/0303832 | A1 | 9/2024 | Chen et al. |
| 2024/0307101 | A1 | 9/2024 | Gera et al. |
| 2024/0312012 | A1 | 9/2024 | Li et al. |
| 2024/0341861 | A1 | 10/2024 | Wolf et al. |
| 2024/0341910 | A1 | 10/2024 | Wolf et al. |
| 2024/0341911 | A1 | 10/2024 | Elimelech et al. |

FOREIGN PATENT DOCUMENTS

| | | | |
|---|---|---|---|
| CN | 101379412 | A | 3/2009 |
| CN | 103106348 | A | 5/2013 |
| CN | 111915696 | A | 11/2020 |
| CN | 112489047 | A | 3/2021 |
| DE | 202004011567 | U1 | 11/2004 |
| DE | 102004011567 | A1 | 9/2005 |
| DE | 102014008153 | A1 | 10/2014 |
| DE | 202022103168 | U1 | 6/2022 |
| EP | 0933096 | A2 | 8/1999 |
| EP | 1640750 | A1 | 3/2006 |
| EP | 1757974 | A1 | 2/2007 |
| EP | 2119397 | A1 | 11/2009 |
| EP | 2134847 | A2 | 12/2009 |
| EP | 2557998 | A1 | 2/2013 |
| EP | 2823463 | A1 | 1/2015 |
| EP | 2868277 | A1 | 5/2015 |
| EP | 2891966 | A1 | 7/2015 |
| EP | 2963616 | A2 | 1/2016 |
| EP | 3028258 | A1 | 6/2016 |
| EP | 3034607 | A1 | 6/2016 |
| EP | 3037038 | A1 | 6/2016 |
| EP | 3069318 | A1 | 9/2016 |
| EP | 3076660 | A1 | 10/2016 |
| EP | 3121789 | A1 | 1/2017 |
| EP | 3123970 | A1 | 2/2017 |
| EP | 2654749 | B1 | 5/2017 |
| EP | 3175815 | A1 | 6/2017 |
| EP | 3216416 | A1 | 9/2017 |
| EP | 2032039 | B1 | 10/2017 |
| EP | 3224376 | A1 | 10/2017 |
| EP | 3247297 | A1 | 11/2017 |
| EP | 3256213 | A1 | 12/2017 |
| EP | 3306567 | A1 | 4/2018 |
| EP | 3320874 | A1 | 5/2018 |
| EP | 2030193 | B1 | 7/2018 |
| EP | 2225723 | B1 | 2/2019 |

(56) References Cited

FOREIGN PATENT DOCUMENTS

| | | | |
|---|---|---|---|
| EP | 2619622 | B1 | 2/2019 |
| EP | 2892558 | B1 | 4/2019 |
| EP | 3494903 | A1 | 6/2019 |
| EP | 2635299 | B1 | 7/2019 |
| EP | 3505050 | A1 | 7/2019 |
| EP | 2875149 | B1 | 12/2019 |
| EP | 3593227 | A1 | 1/2020 |
| EP | 3634294 | A1 | 4/2020 |
| EP | 3206583 | B1 | 9/2020 |
| EP | 3711700 | A1 | 9/2020 |
| EP | 2625845 | B1 | 3/2021 |
| EP | 3789965 | A1 | 3/2021 |
| EP | 3858280 | A1 | 8/2021 |
| EP | 3913423 | A1 | 11/2021 |
| EP | 3952331 | A1 | 2/2022 |
| EP | 3960235 | A1 | 3/2022 |
| EP | 3635683 | B1 | 7/2022 |
| EP | 3602492 | B1 | 11/2022 |
| EP | 4173590 | A1 | 5/2023 |
| EP | 3533031 | B1 | 8/2023 |
| EP | 4252695 | A1 | 10/2023 |
| EP | 3195257 | B1 | 11/2023 |
| EP | 3405909 | B1 | 11/2023 |
| EP | 4270313 | A1 | 11/2023 |
| EP | 4287120 | A1 | 12/2023 |
| EP | 3488381 | B1 | 2/2024 |
| EP | 3834768 | B1 | 2/2024 |
| EP | 3903714 | B1 | 2/2024 |
| EP | 4336450 | A1 | 3/2024 |
| EP | 3814984 | B1 | 4/2024 |
| EP | 4115389 | B1 | 4/2024 |
| EP | 3752981 | B1 | 5/2024 |
| EP | 4375948 | A1 | 5/2024 |
| EP | 4383203 | A1 | 6/2024 |
| GB | 2507314 | A | 4/2014 |
| IL | 262864 | A | 3/2019 |
| JP | 2004-237092 | A | 8/2004 |
| JP | 2008-507361 | A | 3/2008 |
| JP | 2009-514571 | A | 4/2009 |
| JP | 2021-525186 | A | 9/2021 |
| KR | 10-2014-0120155 | A | 10/2014 |
| WO | 03/34705 | A2 | 4/2003 |
| WO | 2006/002559 | A1 | 1/2006 |
| WO | 2007/051304 | A1 | 5/2007 |
| WO | 2007/115826 | A2 | 10/2007 |
| WO | 2008/103383 | A1 | 8/2008 |
| WO | 2010/067267 | A1 | 6/2010 |
| WO | 2010/074747 | A1 | 7/2010 |
| WO | 2012/061537 | A2 | 5/2012 |
| WO | 2012/101286 | A1 | 8/2012 |
| WO | 2013/112554 | A1 | 8/2013 |
| WO | 2014/014498 | A1 | 1/2014 |
| WO | 2014/024188 | A1 | 2/2014 |
| WO | 2014/037953 | A2 | 3/2014 |
| WO | 2014/113455 | A1 | 7/2014 |
| WO | 2014/125789 | A1 | 8/2014 |
| WO | 2014/167563 | A1 | 10/2014 |
| WO | 2014/174067 | A1 | 10/2014 |
| WO | 2015/058816 | A1 | 4/2015 |
| WO | 2015/061752 | A1 | 4/2015 |
| WO | 2015/109145 | A1 | 7/2015 |
| WO | 2016/151506 | A1 | 9/2016 |
| WO | 2018/052966 | A1 | 3/2018 |
| WO | 2018/073452 | A1 | 4/2018 |
| WO | 2018/200767 | A1 | 11/2018 |
| WO | 2018/206086 | A1 | 11/2018 |
| WO | 2019/083431 | A1 | 5/2019 |
| WO | 2019/135209 | A1 | 7/2019 |
| WO | 2019/161477 | A1 | 8/2019 |
| WO | 2019/195926 | A1 | 10/2019 |
| WO | 2019/210353 | A1 | 11/2019 |
| WO | 2019/211741 | A1 | 11/2019 |
| WO | 2020/109903 | A1 | 6/2020 |
| WO | 2020/109904 | A1 | 6/2020 |
| WO | 2021/017019 | A1 | 2/2021 |
| WO | 2021/019369 | A1 | 2/2021 |
| WO | 2021/021979 | A2 | 2/2021 |
| WO | 2021/023574 | A1 | 2/2021 |
| WO | 2021/046455 | A1 | 3/2021 |
| WO | 2021/048158 | A1 | 3/2021 |
| WO | 2021/061459 | A1 | 4/2021 |
| WO | 2021/062375 | A1 | 4/2021 |
| WO | 2021/073743 | A1 | 4/2021 |
| WO | 2021/087439 | A1 | 5/2021 |
| WO | 2021/091980 | A1 | 5/2021 |
| WO | 2021/112918 | A1 | 6/2021 |
| WO | 2021/130564 | A1 | 7/2021 |
| WO | 2021/137752 | A1 | 7/2021 |
| WO | 2021/141887 | A1 | 7/2021 |
| WO | 2021/145584 | A1 | 7/2021 |
| WO | 2021/154076 | A1 | 8/2021 |
| WO | 2021/183318 | A2 | 9/2021 |
| WO | 2021/188757 | A1 | 9/2021 |
| WO | 2021/255627 | A1 | 12/2021 |
| WO | 2021/257897 | A1 | 12/2021 |
| WO | 2021/258078 | A1 | 12/2021 |
| WO | 2022/009233 | A1 | 1/2022 |
| WO | 2022/053923 | A1 | 3/2022 |
| WO | 2022/079565 | A1 | 4/2022 |
| WO | 2023/003952 | A1 | 1/2023 |
| WO | 2023/281395 | A1 | 1/2023 |
| WO | 2023/007418 | A1 | 2/2023 |
| WO | 2023/011924 | A1 | 2/2023 |
| WO | 2023/021448 | A1 | 2/2023 |
| WO | 2023/021450 | A1 | 2/2023 |
| WO | 2023/021451 | A1 | 2/2023 |
| WO | 2023/026229 | A1 | 3/2023 |
| WO | 2023/047355 | A1 | 3/2023 |
| WO | 2023/072887 | A1 | 5/2023 |
| WO | 2023/088986 | A1 | 5/2023 |
| WO | 2023/158878 | A1 | 8/2023 |
| WO | 2023/159104 | A2 | 8/2023 |
| WO | 2023/161848 | A1 | 8/2023 |
| WO | 2023/163933 | A1 | 8/2023 |
| WO | 2023/175244 | A1 | 9/2023 |
| WO | 2023/186996 | A1 | 10/2023 |
| WO | 2023/202909 | A1 | 10/2023 |
| WO | 2023/205212 | A1 | 10/2023 |
| WO | 2023/205896 | A1 | 11/2023 |
| WO | 2023/209014 | A1 | 11/2023 |
| WO | 2023/229415 | A1 | 11/2023 |
| WO | 2023/232492 | A1 | 12/2023 |
| WO | 2023/240912 | A1 | 12/2023 |
| WO | 2024/001140 | A1 | 1/2024 |
| WO | 2024/002620 | A1 | 1/2024 |
| WO | 2024/013642 | A2 | 1/2024 |
| WO | 2024/018368 | A2 | 1/2024 |
| WO | 2024/046760 | A1 | 3/2024 |
| WO | 2024/052136 | A1 | 3/2024 |
| WO | 2024/077077 | A1 | 4/2024 |
| WO | 2024/121060 | A1 | 6/2024 |
| WO | 2024/132609 | A1 | 6/2024 |
| WO | 2024/145341 | A1 | 7/2024 |
| WO | 2024/160896 | A1 | 8/2024 |
| WO | 2024/165508 | A1 | 8/2024 |
| WO | 2024/173251 | A1 | 8/2024 |
| WO | 2024/186811 | A1 | 9/2024 |

OTHER PUBLICATIONS

Everysight, Installing your RX Adaptor, accessed Mar. 13, 2024 at https://support.everysight.com/hc/en-us/articles/115000984571-Installing-your-RX-Adaptor.

Everysight, Raptor User Manual, copyright 2017, in 46 pages.

Frames Direct, InSpatialRx Prescription Insert, Prescription Insert for Magic Leap 1, accessed Mar. 8, 2024 at https://www.framesdirect.com/inspatialrx-prescription-insert. html.

International Search Report and Written Opinion received for PCT Patent Application No. PCT/IB2022/056986, mailed on Dec. 5, 2022, 10 pages.

(56) References Cited

OTHER PUBLICATIONS

Reddit, Notice on Prescription Lenses for Nreal Glasses, accessed Mar. 13, 2024 at https://www.reddit.com/r/nreal/comments/x1fte5/notice_on_prescription_lenses_for_nreal_glasses/.
Vuzix Blades, Prescription Lens Installation Guide, copyright 2020.

* cited by examiner

ROTATING MARKER AND ADAPTER FOR IMAGE-GUIDED SURGERY

FIELD

The present disclosure relates generally to a marker and a marker adapter for image-guided surgery, and particularly to a marker that may be attached to a patient and/or to a marker adapter that allows multiple orientations of a marker.

BACKGROUND

During image guided surgery, it is important to register elements of a patient, upon whom the surgery is being performed, with equipment generating the image. This is typically the case where the surgery comprises an augmented reality system, which generates images of portions of the patient that are in registration with the actual portions.

In order to register the elements of the patient, and keep the registration, a patient marker may be fixedly attached to the patient. An initial image of a marker may be analyzed, and used to provide the registration. So long as a marker continues to be fixedly attached to the patient at the same location, the registration remains valid and may be used to track the patient. However, if the marker is moved and then re-attached, for example to provide access to the patient, the registration typically needs to be repeated.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY

An embodiment of the present disclosure provides a patient marker for image guided surgery that is configured to be coupled to an anchoring device via a base, the base having a base axis, base connections and a first indicator, the patient marker including:

- an adapter having a first surface having first surface adapter connections configured to mate with the base connections, and a second surface, opposite the first surface, having second surface adapter connections congruent with the base connections, and at least one second indicator; and
- an alignment target, including:
- a target region having an alignment pattern formed thereon; and
- a socket connected to the target region and having socket connections congruent with the first surface adapter connections, so that:
- in a first configuration of the marker, the socket is coupled to the base by mating the first surface adapter connections with the base connections and mating the socket connections with the second surface adapter connections, and
- in a second configuration of the marker, the socket is fit onto the base by mating the socket connections with the base connections,
- whereby an angle of orientation of the alignment target about the base axis is indicated by one of the first indicator and the at least one second indicator.

Typically, in any given configuration of the marker, only one of the first indicator and the at least one second indicator is accessible.

In a disclosed embodiment in the first configuration the alignment target fits to the adapter in a plurality of discrete orientations. The discrete orientations may consist of two orientations at 180° to each other.

In a further disclosed embodiment in the second configuration the alignment target fits to the base in a plurality of discrete orientations. The discrete orientations may consist of two orientations at 180° to each other.

In a yet further disclosed embodiment in the first configuration the angle of orientation includes a first pair of angles at 180° to each other, and in the second configuration the angle of orientation includes a second pair of angles at 180° to each other and at 90° to the first pair of angles.

In an alternative embodiment the base connections and the first surface adapter connections are configured so that the adapter mates with the base in one single orientation.

In a further alternative embodiment the at least one second indicator is a divot that acts as a verification point.

In a yet further alternative embodiment the at least one second indicator is formed as an extension of a surface of the adapter.

In a still further alternative embodiment one of the at least one second indicator is positioned so that it aligns with and prevents access to the first indicator, while the first surface adapter connections are mated with the base connections.

The at least one second indicator may consist of two indicators. The angle between lines from each of the two indicators to a central hole of the adapter may be obtuse.

The at least one second indicator may be configured to be touched by a tip of a tool used in the surgery.

There is further provided, according to an embodiment of the present disclosure, a method for producing a patient marker to be coupled to an anchoring device via a base, the base having a base axis, base connections and a first indicator, the method including:

- configuring first surface adapter connections of an adapter having a first surface to mate with the base connections;
- forming on a second surface of the adapter, opposite the first surface, second surface adapter connections congruent with the base connections, and at least one second indicator; and
- providing an alignment target, consisting of:
- a target region having an alignment pattern formed thereon, and
- a socket connected to the target region and having socket connections congruent with the first surface connections, so that:
- in a first configuration of the marker, the socket is coupled to the base by mating the first surface adapter connections with the base connections and mating the socket connections with the second surface adapter connections, and
- in a second configuration of the marker, the socket is fit onto the base by mating the socket connections with the base connections,
- whereby an angle of orientation of the alignment target about the base axis is indicated by one of the first indicator and the at least one second indicator.

There is further provided, according to an embodiment of the present disclosure, an adapter for providing additional orientations to a patient marker with respect to an anchoring device in image guided surgery, wherein the anchoring device has a base having a base axis and a first indicator, the adapter including:

a first surface configured to be coupled to the base;

a second surface, opposite the first surface, configured to be coupled to the patient marker; and at least one second indicator, wherein the patient marker is coupled to the base by coupling the first surface of the adapter with the base and coupling the patient marker with the second surface of the adapter, and wherein when the patient marker is coupled to the anchoring device via the adapter:

an angle of orientation of the patient marker about the base axis is indicated by only one of the at least one second indicator, and the first indicator is not accessible.

Typically, the at least one second indicator consists of two indicators, and wherein when the patient marker is coupled to the anchoring device via the adapter, only one of the two indicators is accessible. Additionally or alternatively, the at least one second indicator may be configured to be touched by a tip of a tool used in the surgery and serve as a verification point.

There is further provided, in accordance with yet another embodiments of the disclosure, a computerized method for updating a registration between a patient marker and a patient due to a change in the orientation of the patient marker during a medical procedure, wherein the patient marker is coupled to an anchoring device via a an adapter, the adapter is coupled to the anchoring device via a base, the anchoring device is attached to the patient, and the base comprises at least one base indicator, and the adapter comprises at least one adapter indicator. The method includes:

registering the patient marker to the patient;

storing a plurality of distinct orientation values, each orientation value corresponds to a different orientation of the patient marker with respect to the anchoring device and associated with an indicator, wherein the indicator is the at least one base indicator or the at least one adapter indicator, and wherein the orientation value indicates a position of the indicator associated with the orientation value with respect to the patient marker;

tracking the position of a tool marker with respect to the patient marker by capturing images of the patient marker and the tool marker via a camera, wherein the tool marker is attached to a tool used in the medical procedure;

determining a current marker orientation value based on analysis of one or more images of the patient marker and the tool marker;

repeatedly calculating subsequent marker orientation values for images captured by the camera; and if a change in marker orientation value was identified in the subsequent marker orientations with respect to the current marker orientation value, then a change in the patient marker orientation is determined and the registration of the patient marker to the patient is updated accordingly.

In a disclosed embodiment, in any orientation of the patient marker with respect to the anchoring device, only one of the at least one base indicator or the at least one adapter indicator is accessible.

In a further disclosed embodiment, the base comprises base connections, the adapter comprises adapter connections and the patient marker comprises marker connections, and wherein the base connections are used to connect the base to both the patient marker and the adapter, in an alternative manner, and the marker connections are used to connect the patient marker to both the base and the adapter, in an alternative manner.

The present disclosure will be more fully understood from the following detailed description of the embodiments thereof, taken together with the drawings in which:

BRIEF DESCRIPTION OF THE DRA WINGS

Figure 3A:
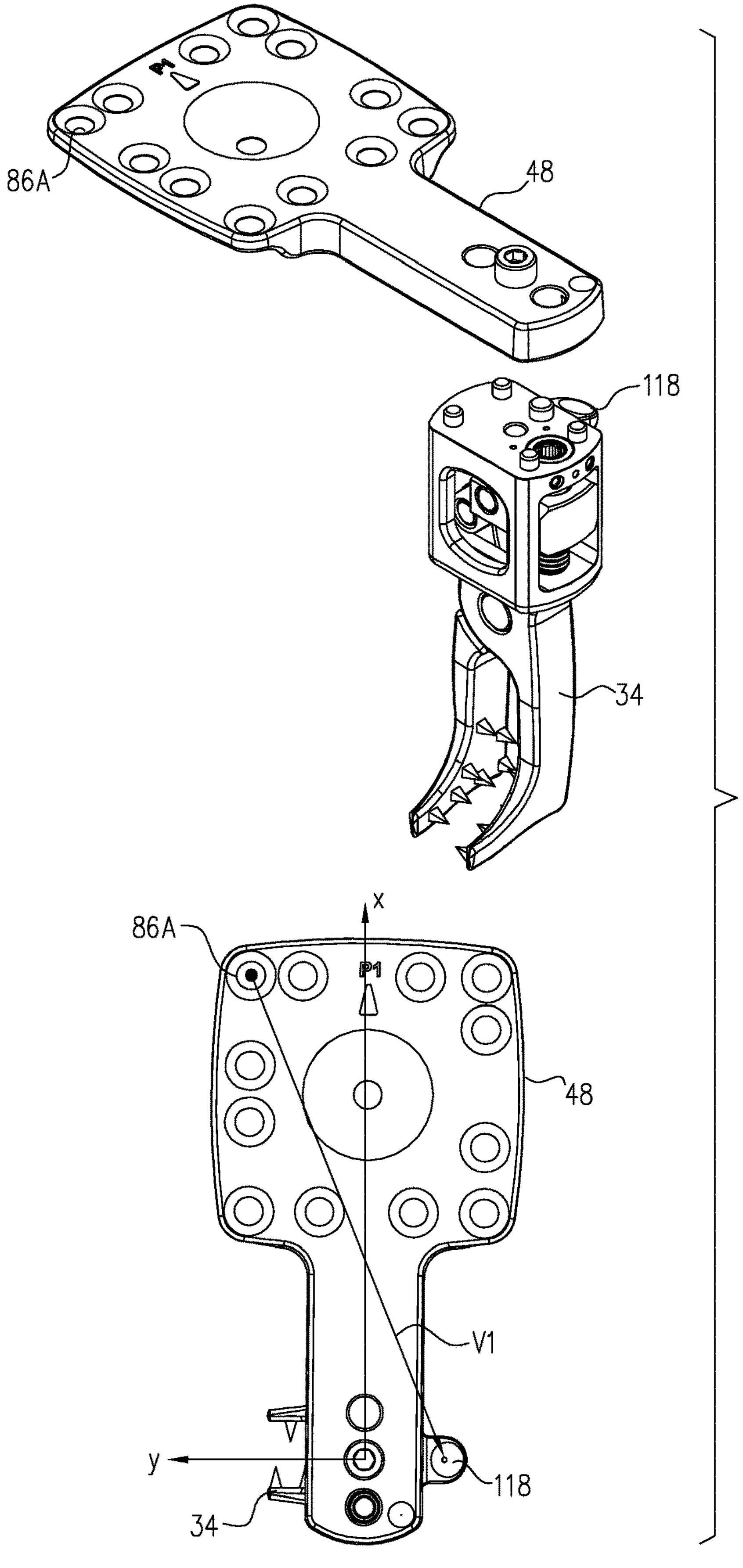
Figure 3B:
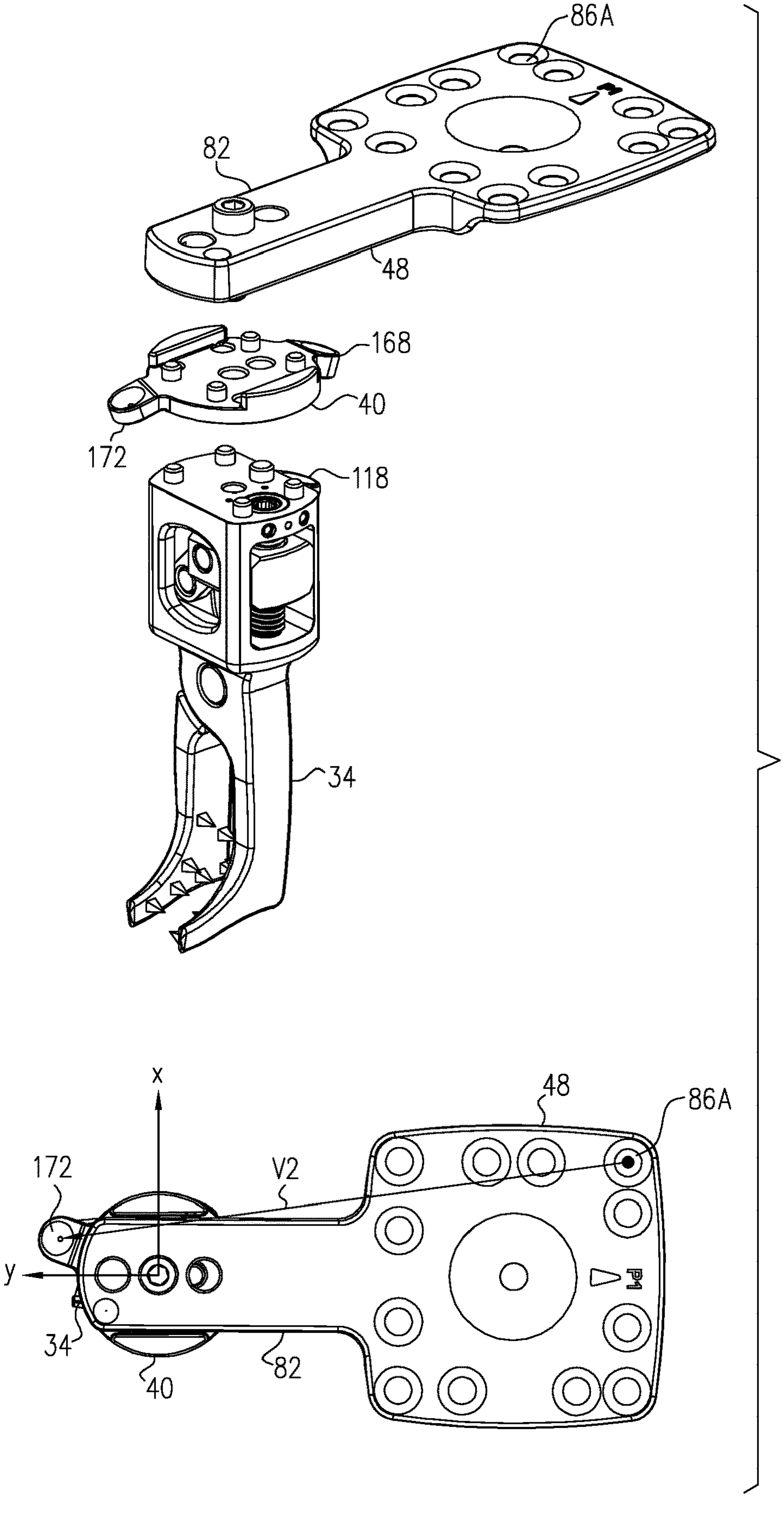
Figure 3C:
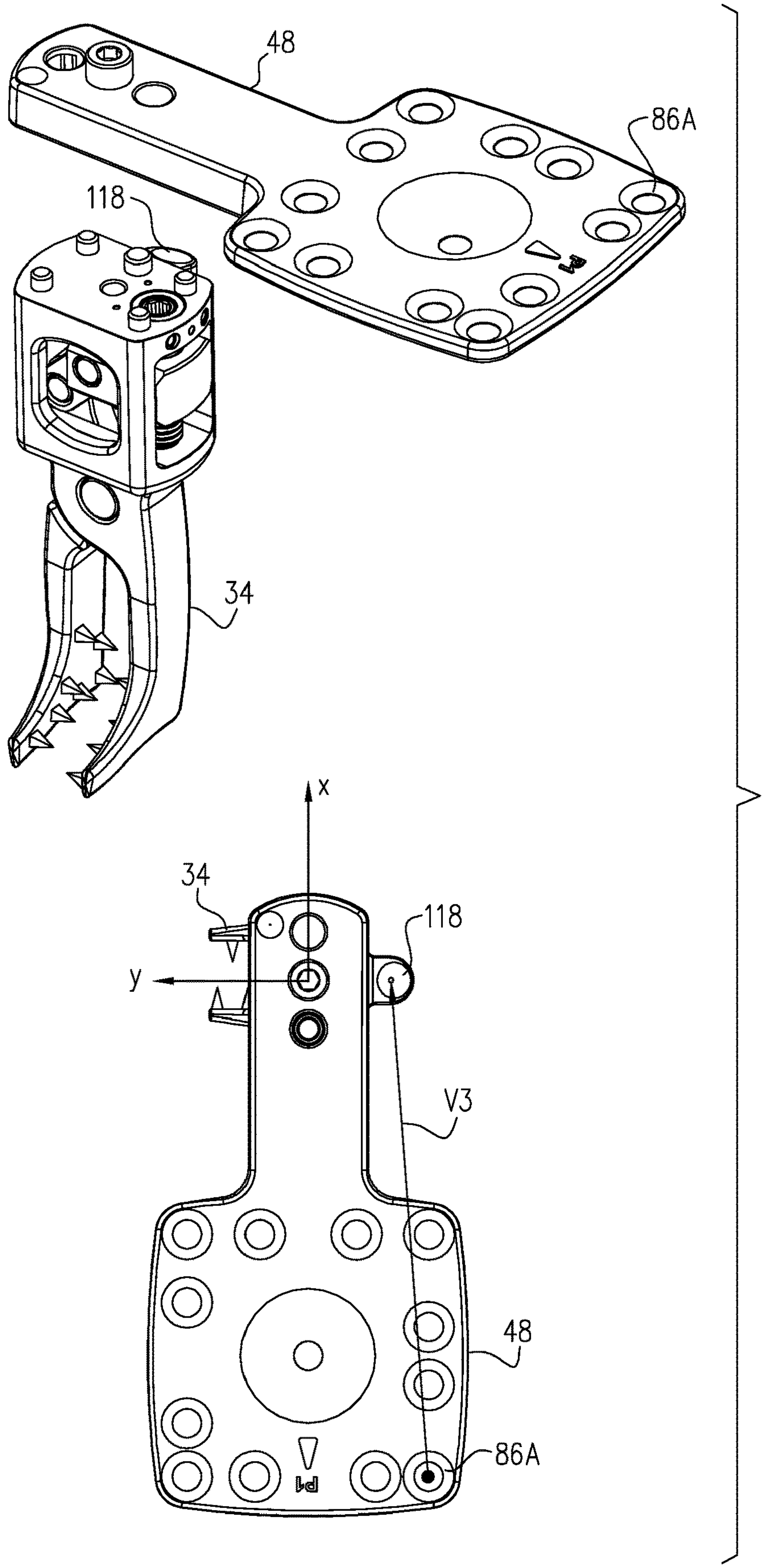
Figure 3D:
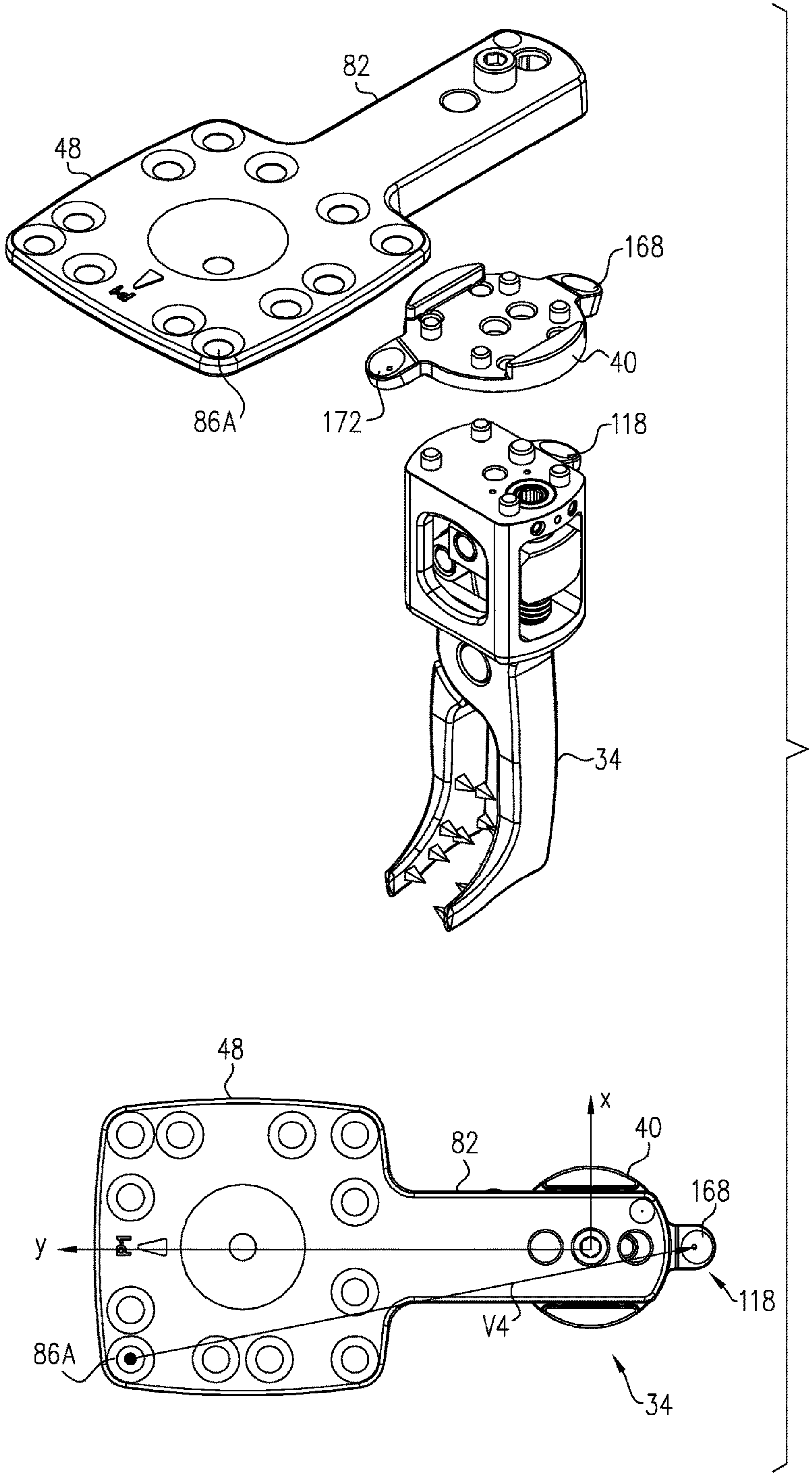
Figure 4:
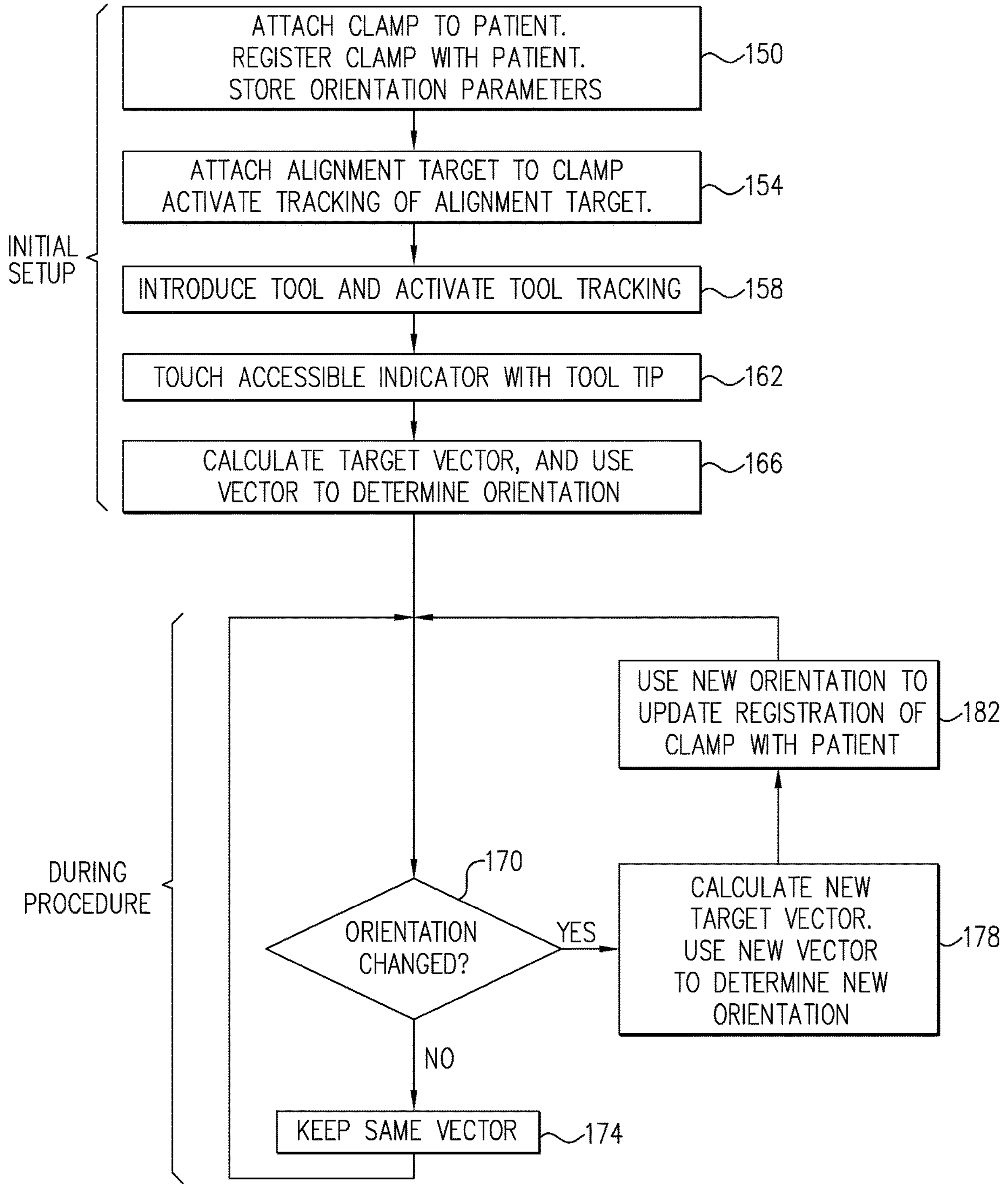
Figure 5A:
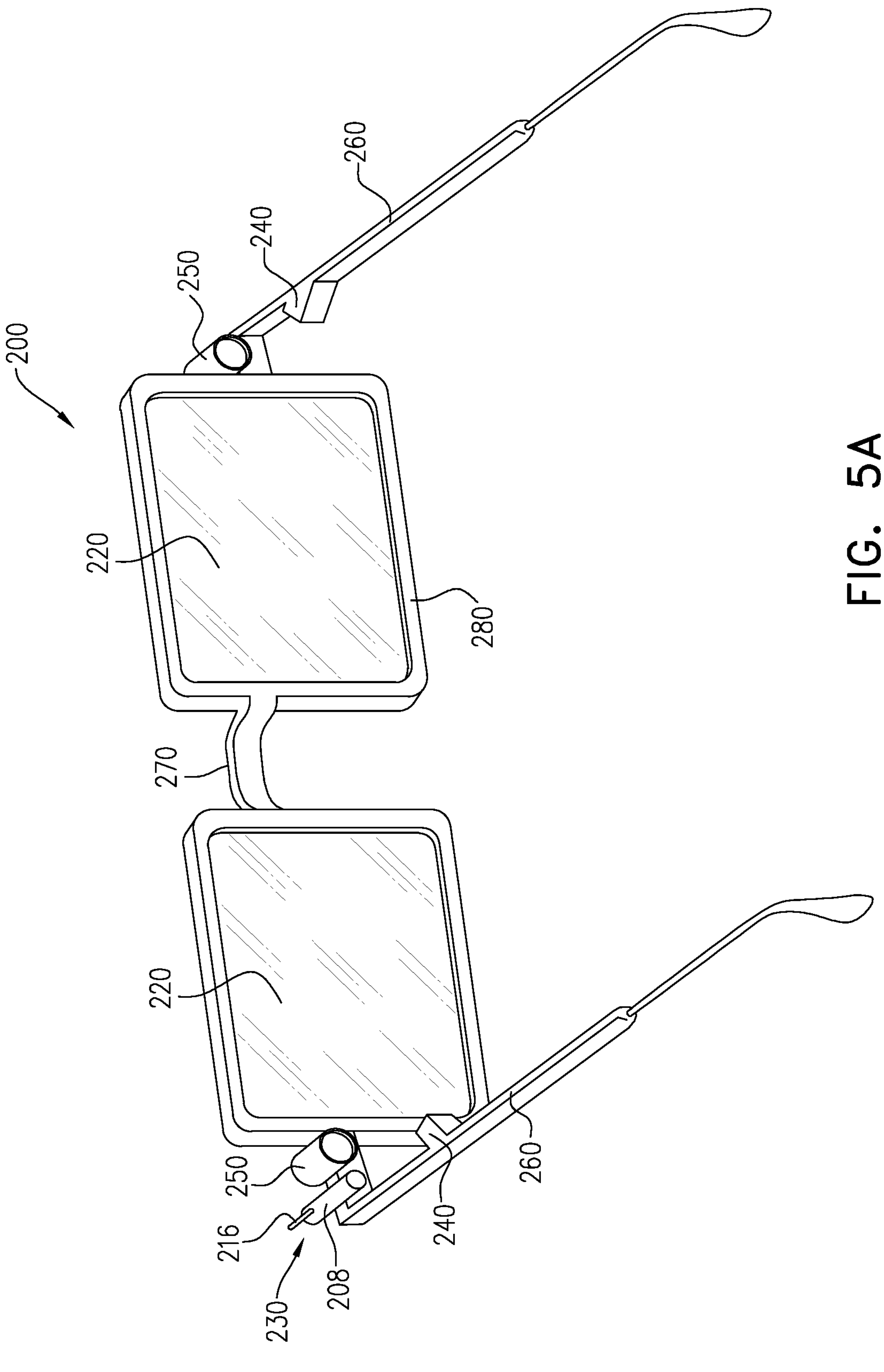
Figure 5B:
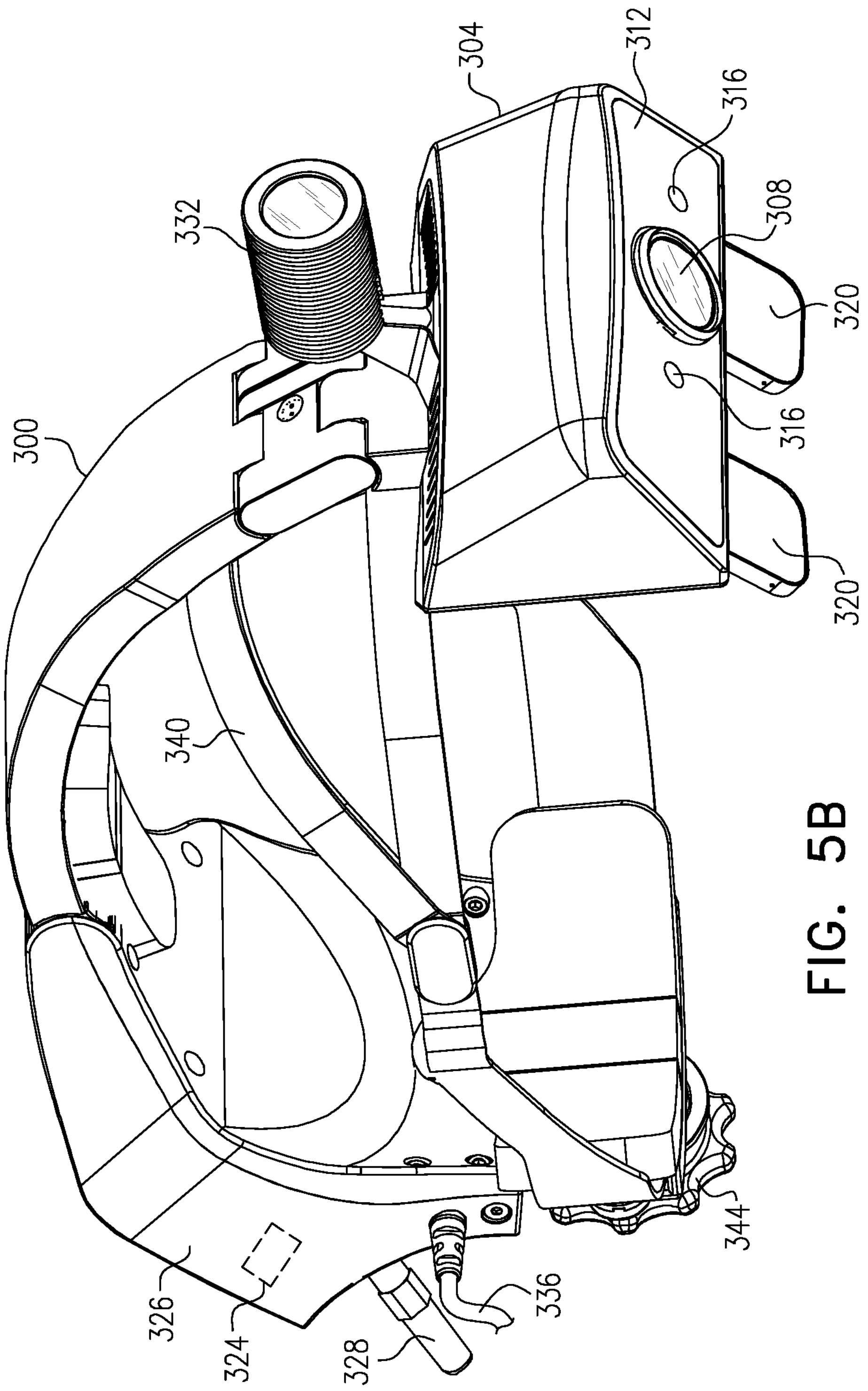

FIGS. 3A, 3B, 3C, and 3D illustrate four orientations of a target of the patient marker with respect to a clamp, according to an embodiment of the present disclosure; and FIG. 4 is a flowchart describing the use of the marker and/or adapter in the medical procedure and a computerized method for updating a registration between a patient marker and a patient due to a change in the orientation of the patient marker during a medical procedure, according to an embodiment of the present disclosure;

FIG. 5A is a schematic illustration of a head-mounted display (HMD), according to an embodiment of the present disclosure;

FIG. 5B is a schematic illustration of a head-mounted display (HMD), according to another embodiment of the present disclosure.

DETAILED DESCRIPTION

Overview

In an augmented reality (AR) system or, generally, in an image-guided system that is used for a medical procedure performed on a patient, the position of the patient, e.g., in relation to an augmented reality assembly worn by a professional performing the procedure, and/or in relation to a tool navigated within the patient body, needs to be tracked. Thus, for example, images presented in the AR assembly or on a display align with the patient and/or are presented from a certain point of view, and/or align with the tool. To implement the tracking, a patient marker, comprising optical elements, may be fixedly attached to the patient, and a camera in the assembly or of an image-guided system may be configured to image the elements. A processor may then analyze the image so as to track the marker. As long as the marker is fixed to the patient, the processor may use the tracking of the marker to track the patient.

However, during the procedure the patient marker may interfere with the professional's access to the patient, and/or the professional's view of the patient, necessitating adjustment of the patient marker.

Embodiments of the present disclosure provide a patient marker which may be adjusted to a plurality of orientations and during a medical procedure, while not requiring any new registration or re-registration and image analysis of the optical elements of a registration marker and the oriented marker to determine their new or adjusted relative position to allow the continuation of the tracking.

Although the use of disclosed embodiments is described with respect to an image-guided system employing AR (e.g., an AR system), the disclosed embodiments may be used, mutatis mutandis, with other image guided systems utilizing optical tracking.

A disclosed embodiment of the present disclosure provides a patient marker comprising a base connecting to an anchoring device such as a pin inserted to a bone or a clamp. The anchoring device herein by way of example assumed to comprise a clamp. Anchoring devices of this sort for image-guided surgery are described, for example, in PCT International Publication WO 2022/079565 and PCT International Application IB2022/056212. The disclosures of all these patent applications and publications are incorporated herein by reference. The clamp has jaws configured to grip a bone of the patient, such as a spinous process. Once the jaws have gripped the bone of the patient, the base provides a rigid platform to which may be attached an alignment target that does not move relative to the patient's bone.

The alignment target may be attached, in a first configuration of the marker, directly to the base in one of a first plurality of preselected orientations. In some embodiments, the alignment target may be attached in a first configuration of the marker directly to the base in a single preselected or predetermined orientation. The term "plurality of configuration" may relate hereinafter to one or more configurations, according to the term context. An image of the alignment target may then be acquired by the camera in the augmented reality assembly worn by the professional, e.g., to implement tracking of the target and of the patient. The target may be adjusted between the first plurality of preselected orientations, without requiring any new registration and any image analysis by the processor of the imaged adjusted target and the registration marker, so that the processor may continue the tracking.

To provide further orientations of the target, embodiments of the disclosure provide an adapter. Rather than attaching the target directly to the base, as in the first configuration described above, in a second configuration of the marker the target is attached to the adapter which is then attached to the base. The adapter provides the target with a second plurality of preselected orientations (e.g., one or more additional preselected orientation), different from the first plurality. As for the second configuration, the target may be adjusted between the second plurality of preselected orientations, without requiring any new registration or image analysis of the registration marker and the patient marker or target, so that the processor may continue the tracking. Furthermore, the target may be adjusted between the first plurality of preselected orientations and the second plurality of preselected orientations, without requiring any new registration or such image.

In addition, in some embodiments, the adapter is configured so that the first and second plurality of preselected orientations are simply related. In a disclosed embodiment the first plurality of configurations, which does not use the adapter, provides a first orientation wherein the target rotates 0° about a base axis and a second orientation wherein the target rotates 180° about the axis. The second plurality of configurations, which uses the adapter, provides a third orientation where the target rotates 90° about the axis and a fourth orientation where the target rotates 270° about the axis. Since the alignment target may be attached, with or without use of the adapter, to the base in a multiplicity of preselected orientations, embodiments of the disclosure provide a simple and cost effective solution for adjusting the patient marker and without requiring new registration and image analysis of the target of the patient marker and the registration marker.

According to some aspects, an adapter, as described above, is provided, which allows further orientations to a marker. The adapter provides additional orientations to the patient marker with respect to the anchoring device. The base (referred to above) connecting to the anchoring device, or comprised in the anchoring device, may be provided by the anchoring device, and the base has a base axis and at least a first indicator. In some embodiments, the base may comprise more than one indicator.

The adapter has two surfaces: a first surface that may be coupled to the base, e.g., by the first surface adapter connections, and a second surface, opposite the first surface, that may be coupled to the patient marker, e.g., via the second surface adapter connections. The adapter also has at least one, e.g., two, second indicators. The patient marker may be coupled to the base by coupling the first adapter surface to the base, and coupling the second adapter surface to the patient marker, so that the patient marker couples to the anchoring device via the adapter.

In each orientation, only one indicator is accessible to prevent confusion and to allow unambiguous determination of the orientation. When the patient marker is coupled to the anchoring device via the adapter, as described above, the angle of orientation of the patient marker about the base axis is indicated by only one of the second indicators. For example, in case of two adapter indicators, when the marker is coupled to the adapter, only one indicator is accessible while the other is covered by the marker (e.g., positioned beneath the marker as exemplified in FIGS. 3B and 3D). Furthermore, the first indicator is not accessible (e.g., covered by the adapter, as shown in FIGS. 3B and 3D).The adapter may be coupled to the anchoring device via its base and may be coupled to the marker; it may be formed, configured to and operate, all as detailed herein above and herein below, with the necessary changes.

During the medical procedure, in addition to tracking the patient marker, a position of the tip of a tool used in the procedure is also tracked. The base of the anchoring device has a verification point or divot fixedly located, in a known preselected position in the base. The adapter also has at least one, and herein by way of example two verification points, fixedly located in known preselected positions on the adapter.

To identify, during the procedure, which of the preselected orientations of the target is operative, the tool tip is placed on, or in proximity to, one of the verification points of the base or the adapter. The processor of the augmented reality system calculates the location of the indicated verification point with respect or relative to the tracked alignment target or patient marker, e.g., by calculating a vector between the indicated verification point and the tracked alignment target, and from that calculated location or vector (which are different for all the target orientations) identifies the orientation of the target or patient marker.

Detailed Description

In the following, all directional references (e.g., upper, lower, upward, downward, left, right, top, bottom, above, below, vertical, and horizontal) are only used for identification purposes to aid the reader's understanding of the present disclosure, and do not create limitations, particularly as to the position, orientation, or use of embodiments of the disclosure.

Figure 1:
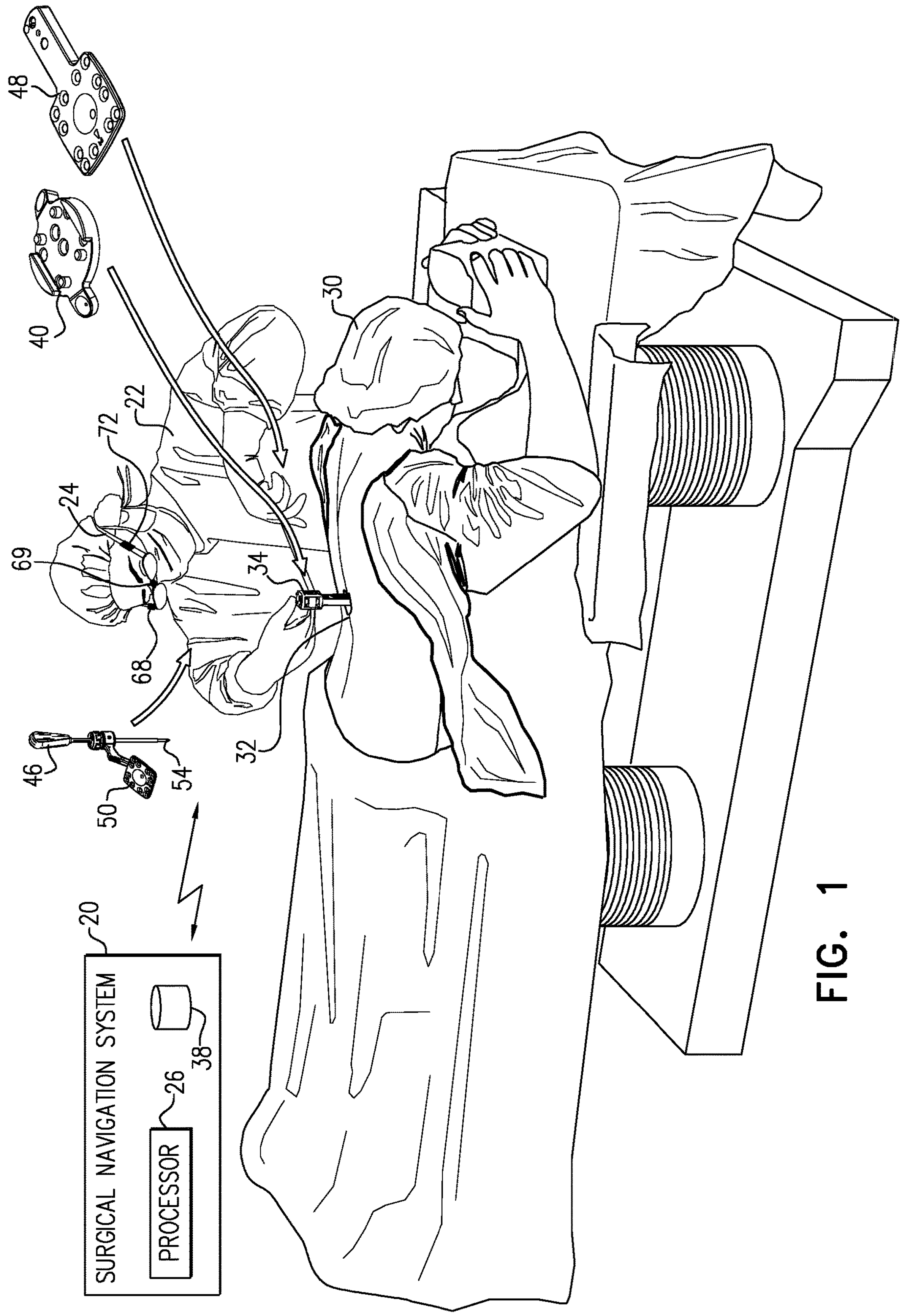
FIG. 1 is a schematic illustration of a medical procedure, according to an embodiment of the present disclosure.

Reference is now made to FIG. 1, which is a schematic illustration of a medical procedure, according to an embodiment of the present disclosure. During the procedure, performed by a professional 22, the professional uses a surgical navigation system 20, which assists the professional in performance of the procedure. Surgical navigation system 20 comprises a processor 26, which operates elements of the system, and which communicates with an augmented reality assembly 24, comprising a set of augmented reality spectacles worn by professional 22, and that is incorporated in the system. Assembly 24 comprises an imaging device. The imaging device may comprise one or more imaging devices. The imaging device is configured, inter alia, to track one or more elements, such as marker 48 or a medical tool used during the procedure. Assembly 24 comprises, for example, an image capturing device 72, also termed herein a camera 72, that has a field of view and that is configured to capture images in the visible spectrum. Assembly 24 also comprises an image capturing device 68, also termed a camera 68, that is operative in the non-visible spectrum, typically the infrared, as well as a projector 69 that projects radiation in the operative spectrum of device 68. Functions of system 20, processor 26, and devices 68 and 72 are described below. Assemblies similar to augmented reality assembly 24, and its operation, are described in U.S. Pat. No. 9,928,629, to Benishti, et al., and PCT International Publication WO 2022/053923 whose disclosures are incorporated herein by reference.

It will be understood that the present disclosure includes augmented reality assemblies other than assembly 24 described here. Examples of such assemblies are described with reference to FIGS. 5A and 5B, and all such assemblies are assumed to be comprised within the scope of the present disclosure.

processor 26 may include one or more processing units. In one embodiment processor 26 is assumed to be incorporated within a stand-alone computer, and the processor typically communicates with other elements of the system, including assembly 24, wirelessly, as is illustrated in FIG. 1. Alternatively or additionally, processor 26 may use optical and/or conducting cables for the communication. In further alternative embodiments processor 26 is integrated within assembly 24, or in the mounting of the assembly. According to an embodiment, processor 26 includes two processing units, while one processing unit is integrated within a work station and the other is integrated within assembly 24. Processor 26 is typically able to access a database 38, wherein are stored images and other visual elements used by system 20. Software enabling processor 26 to operate system 20 may be downloaded to the processor in electronic form, over a network, for example. Alternatively or additionally, the software may be provided on non-transitory tangible media, such as optical, magnetic, or electronic storage media.

The medical procedure exemplified here is performed on a patient 30, and during an initial stage of the procedure professional 22 makes an incision 32 into the patient's back. The professional then inserts an anchoring device 34, herein assumed to comprise a spinous process clamp 34, into the incision, so that opposing jaws of the clamp are located on opposite sides of the spinous processes. The professional adjusts the clamp to grip one or more spinous processes, selected by the professional, of the patient. The professional may then attach an orientation adapter 40 to a base 44 (illustrated in FIG. 2A) of the clamp, and an alignment target 48 to the adapter, the target when attached to the base via the adapter optionally operating as a patient marker 52 (illustrated in FIG. 2A). According to some embodiments, patient marker 52 comprises alignment target 48 coupled, as described herein, to base 44. According to some embodiments, patient marker 52 comprises alignment target 48 and may be coupled directly to base 44 or via orientation adapter 40. As is described below, processor 26 tracks alignment target 48 of patient marker 52 (e.g., via camera 68), and the tracking is used by system 20 to determine the position and orientation of patient 30 during the medical procedure.

During the procedure professional 22 uses a tool 46 comprising a tool marker 50. Processor 26 also tracks tool 46 using tool marker 50 attached to the tool, and because the dimensions of the tool and the tool marker are known, the tracking provides the processor with the position of a tool tip 54 of the tool. A tool and tool marker similar to tool 46 and marker 50 are described in U.S. Patent Publication No. 10,939,977 and U.S. Application Publication No. 2022/0071712, which are incorporated herein by reference.

During the procedure, it may be necessary for professional 22 to adjust the position of target 48 or patient marker 52, typically to enable the professional to more easily access elements of patient 30. Embodiments of the present disclosure facilitate such adjustment, by providing a plurality of different discrete orientations of alignment target 48 or marker 52 with respect to clamp 34. Each of the orientations may be identified by processor 26 from an acquired image of target 48 and from the tracked position of tool tip 54, as is described below. In addition, as is described below, once patient marker 52 has been through an initial setup process to align images presented in assembly 24 with patient 30, processor 26 may maintain the image alignment for the different identified orientation changes, by virtue of the fact that dimensions of target 48, adapter 40, and/or base 44 are known.

Figure 2A:
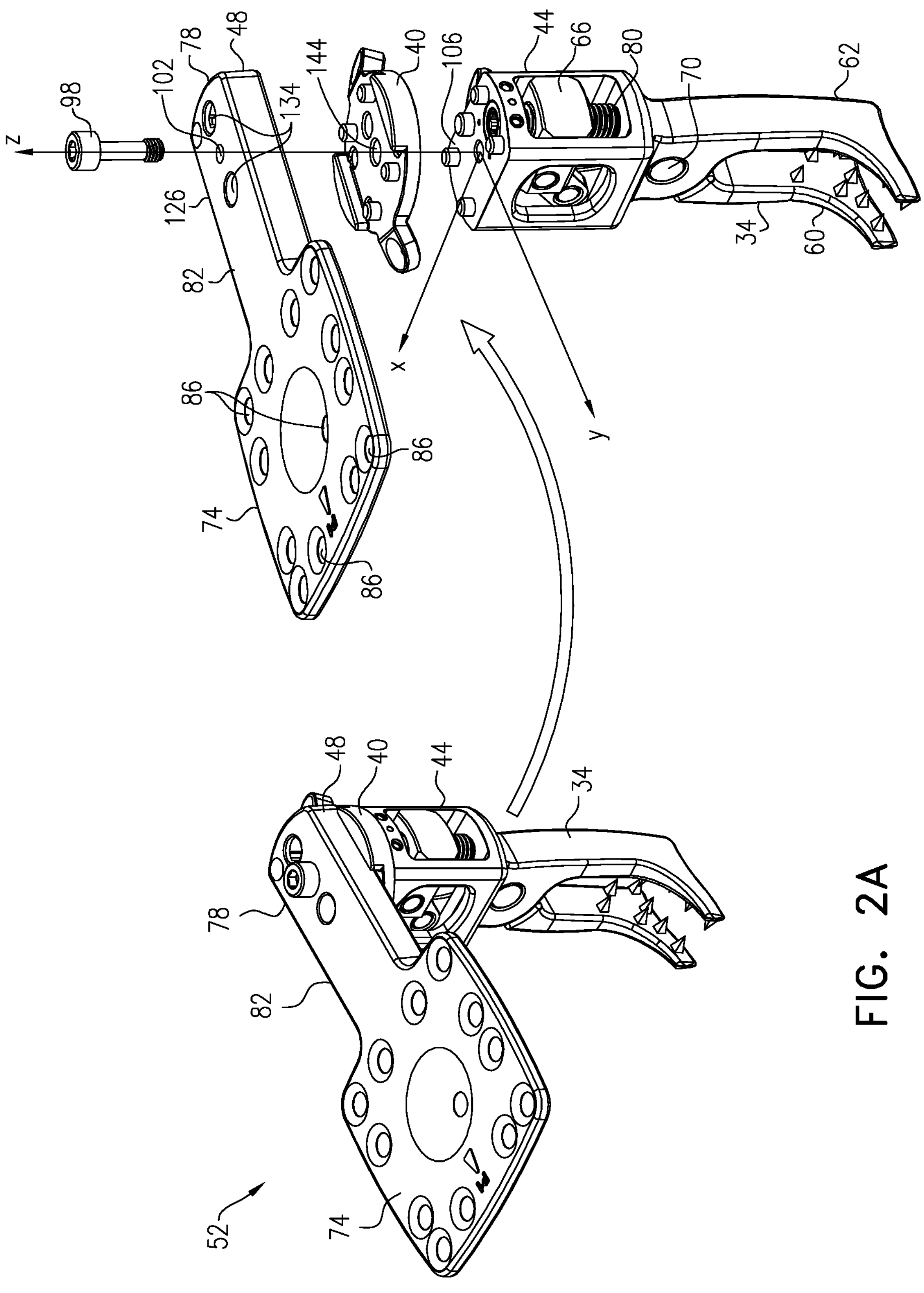
FIG. 2A illustrates elements of a patient marker or an adapter, in an assembled and a partly exploded format.
Figure 2B:
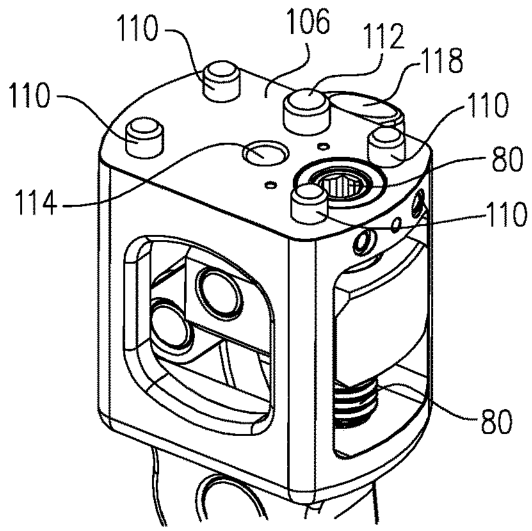
FIGS. 2B, 2C, and 2D illustrate elements of portions of the marker, a base or an adapter, according to embodiments of the present disclosure.
Figure 2C:
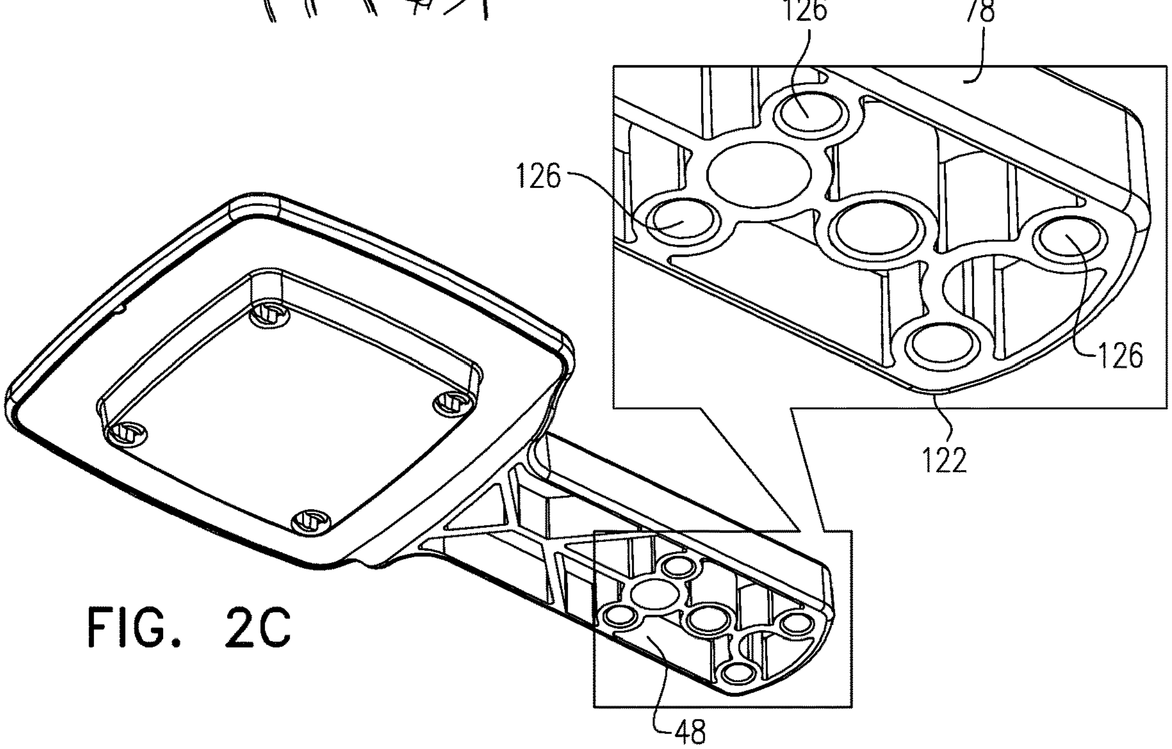
Figure 2D:
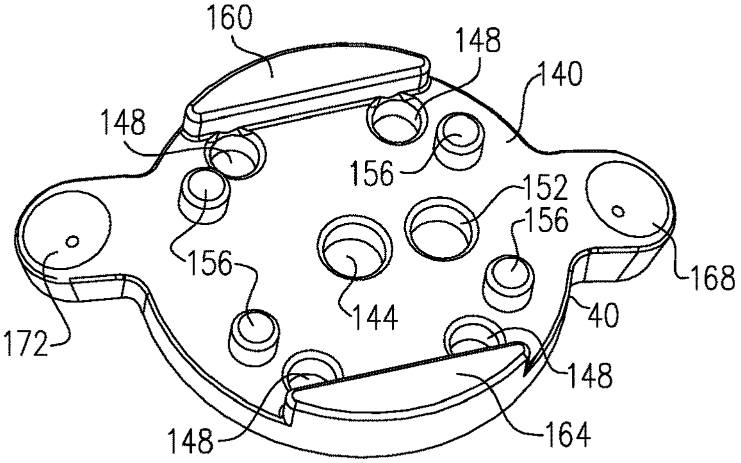

FIG. 2A illustrates elements of patient marker 52 and adapter 40, in an assembled and a partly exploded format, and FIGS. 2B, 2C, and 2D illustrate elements of portions of the marker, the base or the adapter, according to an embodiment of the present disclosure. As stated above, marker 52 may be formed by attaching alignment target 48 to adapter 40, which is in turn attached to base 44 of an anchoring device such as clamp 34. According to aspects of the present disclosure, marker 52, which comprises alignment target 48, may be attached to adapter 40, which may be in turn attached to base 44 of clamp 34. The clamp is described below.

Clamp 34 comprises a pair of jaws 60, 62 in a lower section of the clamp. The jaws are coupled to clamp base 44 in an upper section of the clamp, the base comprising a jaw adjustment mechanism 66. In the embodiment described herein, jaw 62 is fixed to base 44, and jaw 60 moves with respect to jaw 62, by being rotated about a hinge pin 70. Jaw adjustment mechanism 66 comprises an adjustment screw 80, which is coupled by a lever to jaw 60 so that rotation of the screw causes jaw 60 to approach or retreat from jaw 62. Thus professional 22 is able to cause the jaws of clamp 34 to grip or release a bone, such as one or more spinous processes, by rotating screw 80.

Alignment target 48 comprises a target region 74 and a socket 78, the target region and the socket being fixedly connected together by a connecting beam 82. Alignment target 48, together with its components target region 74 and socket 78, are generally planar. Target region 74, by way of example, is approximately rectangular, e.g., approximately square, and comprises optical elements 86. Elements 86 are arranged in a three-dimensional (3D) pattern, although in some embodiments the elements may be in a two-dimensional (2D) pattern, with no rotational axis of symmetry (other than a trivial axis of symmetry for rotating by 360°), and no mirror plane of symmetry, so that an image of the elements enables an unambiguous determination of the location and orientation of the target region. Elements 86 are typically retroreflectors. An entity with an arrangement of optical elements similar to the arrangement herein is described in U.S. Patent Publication No. 10,939,977, which is incorporated hereinabove by reference.

For clarity, in the description herein, elements of marker 52 are assumed, by way of example, to be referenced to a Cartesian set of orthogonal xyz axes, with origin at the center of an upper plane surface 106 of base 44, as illustrated in FIG. 2A. A z-axis is assumed to be orthogonal to plane surface 106, a y-axis is assumed to be parallel to a symmetry axis of hinge 70, and an x-axis is assumed to be orthogonal to the y and z axes. As another example, the origin may be at the center of an optical element 86A of marker 52.

As stated above, socket 78 is generally planar, and has a central hole 102. As is explained below, socket 78 and adapter 40 are fixed to base 44 by a captive screw 98 that penetrates a socket central hole 102 and also an adapter central hole 144. Holes 102 and 144 are dimensioned as clearance holes for screw 98.

FIG. 2B illustrates upper surface 106 of base 44. Surface 106 comprises a threaded hole 114 at the center of the surface, that accepts screw 98. Surface 106 also comprises four substantially similar cylindrical protuberances 110 located at the corners of a non-square rectangle, and distributed symmetrically about hole 114. As described below, protuberances 110 act as connections for base 44. There is a cylindrical protuberance 112 that in the illustrated embodiment is centered on a longer side of the non-square rectangle, and that is larger than protuberances 110. Extending from base 44, and fixed to the base, is a divot 118 that acts as a verification point or indicator and that is herein also termed divot indicator 118 or just indicator 118. There is an aperture in surface 106 that provides access to screw 80.

FIG. 2C illustrates a lower surface 122 of socket 78, and an upper surface of the socket is shown in FIG. 2A. Lower surface 122 comprises four cylindrical recesses 126 that are dimensioned and positioned to accept protuberances 110 of surface 106, when socket 78 is placed on surface 106, so that recesses 126 also act as connections. An upper surface 126 of the socket comprises two access holes 134, distributed symmetrically about clearance hole 102. In addition, when socket 78 is mated with surface 106, clearance hole 102 aligns with threaded hole 114, so that screw 98 may be used to attach the socket, and thus the target, to base 44.

The description above, of target 48 being directly attached to surface 106, i.e., without adapter 40 being used, corresponds to a first configuration of marker 52. It will be understood that because the connection between the base and the marker has a rotational symmetry which is a rectangular rotational symmetry (i.e., of 180°), e.g., of recesses 126 and protuberances 110, there are two possible orientations of the target (e.g., target 48) or marker (e.g., marker 52) with respect to the anchoring device (e.g., clamp 34), when the target or marker is attached to the base (e.g., base 44) in this first configuration. A partially exploded view of each orientation is exemplified in FIG. 3A and FIG. 3C.

In some embodiments, the connection between the target or the marker and the base may not have a rotational symmetry and thus may allow only one single orientation with respect to the anchoring device or with respect or the anchoring device base. In some embodiments, the connection between the target or the marker and the base may have a square rotational symmetry (i.e., of 90°) which may allow up to four orientations with respect to the anchoring device or with respect to its base. Thus, the connection and connection elements may be defined and accordingly formed to allow various rotational symmetries with may allow various maximal orientations, correspondingly.

In some embodiments, the target-base, marker-base, target-adapter or marker-adapter connection rotational symmetry may be around an axis perpendicular to the plane of the upper surface of the base, such as surface 106, and located at its center, such as hole 114 of surface 106. Z axis of FIG. 2A is an example for such a connection rotational symmetry axis.

FIG. 2D illustrates an upper surface 140 of adapter 40. Adapter 40 is generally circular, but may be of other shapes (e.g., rectangular), and clearance hole 144 is located at the center of the adapter. Adapter 40 comprises four cylindrical holes 148 that are dimensioned and positioned to accept protuberances 110 of surface 106, when the adapter is placed on surface 106. Holes 148 are distributed symmetrically about central clearance hole 144, and it will be understood that holes 148 form a non-square rectangle. Holes 148 penetrate to a lower surface of adapter 40, and act as connections. To enable a single non-ambiguous placement of the adapter, the adapter also comprises a fifth cylindrical hole 152, that is dimensioned and positioned to accept protuberance 112 when holes 148 connect with, i.e., mate with, protuberances 110.

Four cylindrical protuberances 156 are formed on surface 140, and they are arranged to be congruent to protuberances 110, and thus lie in a non-square rectangle. Protuberances 156 are distributed symmetrically about central hole 144, and are located so that the non-square rectangle they form is orthogonal to the non-square rectangle formed by holes 148. As for protuberances 110, protuberances 156 act as connections.

According to some embodiments of the present disclosure and as shown in FIGS. 2A-2D, the target or marker connections or connection elements used to connect the target or marker to the base are also used to connect the target or marker to the adapter and in a substantially similar manner. Thus, the connection between the adapter and the target or the marker has the same connection rotational symmetry as the connection between the target or the marker and the base. Accordingly, the maximal number of additional different marker orientations which may be allowed by the adapter is equal to the maximal number of marker orientations which may be allowed by the rotational symmetry of the connection between the base and the target or marker.

According to some embodiments and as shown in FIGS. 2A-2D, the connection between the target or marker and the base and/or the connection between the target or marker and the adapter are such that the adjustment or change of an orientation of the target or marker with respect to the base and/or marker is performed by completely disconnecting the marker from the base or from the adapter, and reconnecting it to the base or the adapter in a different orientation with respect to the base and/or adapter.

In operation of marker 52 (illustrated in FIGS. 2A-2D) using adapter 40, the adapter is first placed on surface 106 of base 44 so that holes 148 mate with protuberances 110, and so that hole 152 mates with protuberance 112. It will be understood that for this mating there is only one possible orientation of the adapter with respect to base 44, and that in this orientation clearance hole 144 aligns with threaded hole 114 of the base.

Once adapter 40 has been placed on surface 106, socket 78 of target 48 may be mated with the upper surface of the adapter, by pushing recesses 126 of the socket onto protuberances 156. In some embodiments, the mating is facilitated by forming retaining shoulders 160, 164 on the surface of the adapter, symmetrically on either side of hole 144, the shoulders having internal walls that are separated by the width of socket 78, together with a clearance value. In some embodiments, retaining one or more shoulders such as retaining shoulders 160 of adapter 40 may limit the number of orientations (e.g., to two orientations, as in adapter 40, or to a single orientation) and determine the orientations in which a target or a marker, such as target 48 or patient marker 52, may connect to the adapter with respect to the base and/or the adapter. In some embodiments, where the connection or connection elements of the adapter replace the connection or connection elements of the base (e.g., forming the same or substantially the same connection with the marker as the base), one or more such retaining shoulders may be used to prevent the connection of a registration marker, which has a single non-ambiguous predefined location with respect to the anchoring device and/or base, to the adapter. Registration markers of this sort are described, for example, in PCT International Publication WO2021019369. The disclosures of this patent application publication is incorporated herein by reference.

The description above, of target 48 being attached to surface 106 via adapter 40, corresponds to a second configuration of target 48 or marker 52. It will be understood that in this second configuration, there are two possible orientations of target 48 with respect to clamp 34, when the target is attached to adapter 40. A partially exploded view of each orientation of the second configuration is shown in FIG. 3B and FIG. 3D.

First and second divots 168, 172, which act as verification points or indicators and which are also herein termed first and second divot indicators 168, 172, or just indicators 168, 172, are formed in adapter 40 as extensions of surface 140. First indicator 168 is positioned so that it aligns with, and prevents access to, indicator 118 when the adapter is attached to surface 106. Second indicator 172 is positioned so that the angle between a line segment from indicator 172 to central hole 144 and a line segment from indicator 168 to the central hole is an obtuse angle, less than 180°. In a disclosed embodiment the angle is approximately 160°, but other angles are possible. Positioning of second indicator 172 is referred to further below.

As stated above, marker 52 has two possible configurations, and for each configuration target 48 has two possible orientations with respect to clamp 34. There are thus four different orientations of target 48 with respect to the clamp. As is described below, using images of optical elements 86 of target 48, and being provided with the positions of indicators 118, 168, or 172, processor 26 is able to identify in which of the four orientations target 48 is. As is also described below, the processor is able to adjust the images presented to the professional in the augmented reality assembly to compensate for any change in the orientation. FIGS. 3A, 3B, 3C, and 3D illustrate the four possible orientations of target 48 with respect to clamp 34, according to an embodiment of the present disclosure. In each of the figures, marker 52 is drawn as a partially exploded view of the marker, and also as a top-down, i.e., down the z-axis, view of the marker. From consideration of the figures, and of the construction of the elements of marker 52 described above, it will be understood that in each of the four orientations target 48 is rotated clockwise by a multiple of 90° from the x-axis, i.e., in FIG. 3A by 0°, in FIG. 3B by 90°, in FIG. 3C by 180°, and in FIG. 3D by 270°. The orientations are also referred to herein as the 0°, 90°, 180°, and 270° orientation.

In the first configuration of the marker, i.e., when adapter 40 is not used, corresponding to FIGS. 3A and 3C and the 0° and 180° orientations, the only indicator present, and thus accessible, is indicator 118 of base 44.

In the second configuration of the marker, when adapter 40 is used, corresponding to FIGS. 3B and 3D and the 90° and 270° orientations, all three indicators 118, 168, and 172, are present. However, the indicators of adapter 40 are arranged so that only one of indicators 118, 168, and 172 is accessible in each orientation. Thus, in the 90° orientation illustrated in FIG. 3B, indicators 118 and 168 are obscured by connecting beam 82, and only indicator 172 is accessible. In the 270° orientation illustrated in FIG. 3D, indicator 172 is obscured by connecting beam 82, and indicator 168 obscures indicator 118 of base 44, so that only indicator 168 is accessible.

It will be appreciated that in each of the four possible orientations, only one indicator is accessible.

Using the locations of the accessible indicators, for each orientation processor 26 calculates a respective vector from a preselected point on target 48 to the accessible indicator. In the figures, the preselected point is assumed to be an optical element 86 at a corner of target 48, herein termed element 86A, but any other convenient preselected point on the target, such as a center of the target, may be used. As shown in the figures, for orientations 0°, 90°, 180°, and 270° there are respective vectors V1, V2, V3, and V4.

Table I below illustrates the orientations, vectors and parameters associated with the vectors. The vector parameters are assumed to comprise ordered triples, as measured with respect to the xyz axes described above.

TABLE I

| Orientation | Vector | Vector Parameters |
|---|---|---|
| 0° | V1 | $(x_1, y_1, z_1)$ |
| 90° | V2 | $(x_2, y_2, z_2)$ |
| 180° | V3 | $(x_3, y_3, z_3)$ |
| 270° | V4 | $(x_4, y_4, z_4)$ |

Table II below gives a numerical example, according to a disclosed embodiment, of approximate vector parameters, in mm, for the different orientations.

TABLE II

| Orientation | Vector | Vector Parameters |
|---|---|---|
| 0° | V1 | (−103, −42, −13) |
| 90° | V2 | (−17, +124, −8) |
| 180° | V3 | (+103, +8, −13) |
| 270° | V4 | (+25, −126, −8) |

Since the dimensions of all elements of marker 52 and adapter 44 are known, numerical values of the vectors of the different possible orientations may be precalculated and stored by processor 26. The vectors may be stored in any convenient format known in the art, for example related to a cylindrical coordinate system, or to a spherical coordinate system, or to another Cartesian set of axes, rather than the Cartesian axes presented here. All such formats are assumed to be comprised within the scope of the present disclosure.

FIG. 4 is a flowchart describing the use of a marker, such as marker 52 and/or and adapter, such as adapter 40, in the medical procedure referred to above and a computerized method for updating a registration between a patient marker and a patient due to a change in the orientation of the patient marker during a medical procedure, according to an embodiment of the present disclosure.

In an initial step 150, professional 22 attaches clamp 34 or any other anchoring device to a bone of patient 30, herein assumed to comprise a spinous process of the patient, by rotating screw 80. A registration marker is attached to the clamp and the clamp and/or the registration marker is registered to the patient, typically by a CT (computerized tomography) scan. A patient marker, such as patient marker 52, is attached to the clamp in a location with respect to the registration marker which may be predetermined or tracked and calculated. Methods for registering an anchoring device such as a clamp and/or a registration marker and thus a patient marker to a patient is provided in PCT International Publication WO2021019369 incorporated by reference hereinabove and U.S. Patent Application Publication No. 2021-0161614, which is incorporated herein by reference. In the initial step, processor 26 registers the clamp and/or patient marker to the patient and stores the preselected point on the target (referred to above) and distinct orientation value for each marker orientation (e.g., four distinct orientation values for four different marker orientation). The orientation value is determined based on a position of an indicator, associated with the marker orientation, with respect to the marker (e.g., with respect to the preselected point on the target). The orientation value may be a three-dimensional location vector in a predetermined coordinate system (e.g., a coordinate system of the anchoring device or a coordinate system of the marker) determined by vector parameters such the vectors and vector parameters for the four orientations of marker 52, corresponding to the values in Table I.

In a target attachment step 154, the professional uses screw 98 to attach alignment target 48 or patient marker 52 to the clamp, in one of the four orientations illustrated in FIGS. 3A-3D. It will be understood that depending on the orientation selected, the professional may or may not use adapter 40 for the attachment.

Once alignment target 48 is attached to the clamp, camera 68 and projector 69 are activated, so that processor 26 begins to track the alignment target and the preselected point in the target.

In a tool activation step 158, professional 22 introduces tool 46 into proximity with the patient, and initiates tracking of the tool. The tracking uses tool marker 50, and images of the marker generated in camera 68 from radiation of projector 69. The tracking provides processor 26 with the position of tool tip 54. In some embodiments, processor 26 performs the tracking of tool 54 via camera 68.

In an indicator access step 162, professional 22 touches tool tip 54 on the single indicator, i.e., indicator 118, 168, or 172, that is accessible by virtue of the orientation of target 48 formed in step 154. Processor 26 may recognize that the indicator is being touched by any convenient method known in the art, for example by the tool tip being held on, or in proximity to, the indicator for a preselected period of time, and/or by the tool tip being within a preselected region of the tracked alignment target.

In an orientation calculation step 166, from coordinates of the accessible indicator position and of the preselected point position in the tracked alignment target the processor calculates the orientation value, e.g., coordinates of the vector parameters (as in Table I) joining the positions, and from the parameters stored in step 150, identifies the orientation of step 154.

Step 166 completes an initial setup set of steps of the flowchart. The remaining steps are performed as the procedure being performed by professional 26 continues.

Control in the flowchart passes to a decision step 170, where the processor iteratively checks if a change of orientation of the alignment target has occurred. Typically, the change is effected by professional 26 removing then re-attaching the target to clamp 34.

The processor may perform its check by issuing a request, after a preset time period has passed, to the professional to touch tool tip 54 on the single accessible indicator. Alternatively or additionally the professional may inform the processor that a change has been made by any convenient method known in the art, for example by placing tool tip 54 on the single accessible indicator for the preselected period of time referred to above. Alternatively, or additionally the processor may compute a current orientation value, e.g., location vector parameters for the current location of the tool tip with respect to the marker in each image captured by camera 68, or in each preselected number of images, and compare these parameters to the stored parameters to identify if a change of orientation has been made. A stored orientation value will be received for a calculated current orientation value only if the tool tip is located on the indicator associated with the current marker orientation. Once such a stored orientation value is received, the processor may check if this value is different from the previously received stored orientation value which corresponds to the preceding marker orientation. The preceding marker orientation may be the same or different. In some embodiments, a change of orientation is identified based on a sequence of a predefined number of images exhibiting such a change.

If decision step 170 returns negative, i.e., the processor finds there is no change in the target orientation, then in a no change step 174, the processor continues using the existing vector, and control returns to decision step 170.

If decision step 170 returns positive, i.e., the processor finds there is a change in the target orientation then in a change vector step 178 the processor calculates the new coordinates of the new target vector, as described in step 166. The processor uses the new vector to determine the new orientation of the target, and uses the new orientation to continue tracking the target.

In an update registration step 182, the processor uses the new orientation to update the registration of clamp 34 with patient 30. Control then returns to decision step 170.

FIG. 5A is a schematic illustration of a head-mounted display (HMD) 200 in the form of spectacles or glasses, according to an embodiment of the present disclosure. HMD 200 is worn by professional 22, and is similar to and may be used in place of assembly 24 (FIG. 1).

Typically, head-mounted device 200 includes a tracking device 230 that is configured to facilitate determination of the location and orientation of head-mounted device 200 with respect to marker 48 (or patient 30) and/or with respect to tool 46.

Tracking device 230 includes an image-capturing device 208, typically a camera and herein referred to as camera 208, that is configured to image reflective elements 86 (shown in FIG. 2A) of patient marker 52 and reflective elements of tool marker 50. Patient marker 52 and tool marker 50 act as identifying markers for respective entities associated with the markers.

Tracking device 230 includes a light source 216, which is mounted on HMD 200. The light source is typically configured to irradiate the patient marker and the tool marker, such that light reflects from marker reflective elements toward camera 208. For example, light source 216 may be an infrared light source (for example, a light source that generates light at a wavelength of between 700 nm and 800 nm) and the camera may include a corresponding infrared filter. Optionally, HMD 200 may include additional one or more cameras 250, which are configured to capture images of scenes in the visible spectrum.

HMD 200 further comprises a pair of augmented reality displays 220, which allow professional 22 to view entities, such as part or all of patient 30 through the displays, and which are also configured to present to the professional images that may be received from database 38, camera 250 or may present any other information. HMD 200 comprises a frame 280 which, inter alia, holds displays 220 and temples 260. Frame 280 comprises a nose bridge 270.

HMD also includes a processing unit of processor 26 (not shown), which operates elements of the HMD. Alternatively, HMD 200 may comprise processor 26. The processing unit or processor 26 may be mounted on or integrated within frame 280 or temples 260. In some embodiments, the processing unit typically may communicate with other processing units of processor 26, e.g., via an antenna (not shown).

Elements of the HMD are typically powered by a battery (not shown in the figure). HMD 200 is held in place on the head of professional 22 by temples 260 and nose bridge 270.

FIG. 5B is a schematic figure illustrating a head-up display (HUD) or head-mounted display (HMD) 300, according to another embodiment of the present disclosure. HMD 300 is worn by professional 22, and may be used in place of assembly 24 (FIG. 1). HMD 300 comprises an optics housing 304 which incorporates an infrared camera 308. Housing 304 also comprises an infrared transparent window 312, and within the housing, i.e., behind the window, are mounted one or more infrared projectors 316. Mounted on housing 304 are a pair of augmented reality displays 320, which allow professional 22 to view entities, such as part or all of patient 30 through the displays, and which are also configured to present to the professional images that may be received from database 38 or any other information.

The HUD includes a processing unit 324 (or a processing unit of processor 26), mounted in a processor housing 326, which operates elements of the HMD. In some embodiments, processor 324 may communicate with other processing units of processor 26 via an antenna 328.

Mounted on the front of HMD 300 is a flashlight 332. The flashlight projects visible spectrum light onto objects so that professional 22 is able to clearly see the objects through displays 320. Elements of the head-up display are typically powered by a battery (not shown in the figure) which supplies power to the elements via a battery cable input 336.

HUD 300 is held in place on the head of professional 22 by a head strap 340, and the professional may adjust the head strap by an adjustment knob 344.

It will be understood that although the above description specifically refers to a group of discrete orientations comprising the angles of 0°, 90°, 180°, and 270°, those having ordinary skill in the art will be able to adapt the description, mutatis mutandis, for other groups of discrete orientations, such as 0°, 60°, 120°, and 180°, or other groups comprising number of orientation different than four, such as 0°, 120°, 240° or 0°, 60°, 120°, 180°, 240° and 300°, and all such groups are considered to be comprised within the scope of the present disclosure.

It will be understood that although the above description specifically refers to embodiments utilizing three indicators, while the first is comprised in the anchoring device base and the other two are comprised in the adapter, those having ordinary skill in the art will be able to adapt this description, mutatis mutandis, for other embodiments comprising a different number of indicators, or a different arrangement of indicators. For example, in some embodiments only two indicators, one comprised in the base and the other comprised in the adaptor, may be utilized. Each such configuration comprises a group of marker orientations comprising two or more distinct marker orientations and a group of indicators comprising one or more indicators. Each marker orientation is associated with an indicator from the group of indicators. In each marker orientation, only the associated indicator should be accessible to prevent confusion and facilitate simple and non-ambiguous determination of orientation. Each such pair of marker orientation and associated or corresponding indicator should provide a distinct location vector, e.g., determining the location of the indicator relative to the marker in a predefined coordinate system.

While the description above assumes that anchoring device 34 comprises a clamp, it will be understood that the anchoring device may comprise other types of attachment to the bone of patient 30, such as a pin that is inserted into the bone. Such a pin and a pin adapter are disclosed, for example, in PCT International Application IB2022/056212 incorporated by reference hereinabove, while the marker or target or the marker adapter of the present disclosure may be attached to the pin via the pin adapter. Thus, the scope of the present disclosure includes all such types of attachment.

In accordance with several embodiments, processor 26 typically comprises a general-purpose computer processor, which is programmed in software to carry out one or more of the functions described hereinabove and such as registration, tracking, image analysis, orientation values calculation. This software (e.g., executable program instructions) may be stored on tangible, non-transitory computer-readable media, such as optical, magnetic, or electronic memory media. Additionally or alternatively, at least some of the functions of processor 26 may be carried out using special-purpose computing hardware, such as a graphics processing unit (GPU).

It will be appreciated that the embodiments described above are cited by way of example, and that the present disclosure is not limited to what has been particularly shown and described hereinabove. Rather, the scope of the present disclosure includes both combinations and subcombinations of the various features described hereinabove, as well as variations and modifications thereof which would occur to persons skilled in the art upon reading the foregoing description and which are not disclosed in the prior art.

The invention claimed is:

1. A method of updating a registration associated with a patient marker used in a medical procedure, wherein:

the patient marker is coupled to an anchoring device via an adapter, the adapter is coupled to the anchoring device via a base, the anchoring device is attached to a patient, the base comprises at least one base indicator, the adapter comprises at least one adapter indicator, and a tool for use in the medical procedure comprises a tool marker, the method comprising, by at least one processor:

tracking a position of the tool marker with respect to the patient marker by analyzing images, captured by at least one camera, of the patient marker and the tool marker;

detecting that a tip of the tool is in proximity to an accessible indicator of the at least one base indicator or the at least one adapter indicator;

calculating a vector between a preselected point of the patient marker and the accessible indicator;

determining, using the calculated vector, a current patient marker orientation with respect to the anchoring device, by referencing one or more stored vector parameters, wherein the one or more stored vector parameters each correspond to one of a plurality of discrete patient marker orientations with respect to the anchoring device;

checking whether the determined current patient marker orientation is indicative of a change in patient marker orientation; and responsive to determining that a change in patient marker orientation has occurred, updating the registration to correspond to the current patient marker orientation.

2. The method of claim 1, wherein in any of the plurality of discrete patient marker orientations with respect to the anchoring device, only one of the at least one base indicator or the at least one adapter indicator is accessible.

3. The method of claim 1, wherein the base comprises base connections, the adapter comprises adapter connections, and the patient marker comprises marker connections, and wherein the base connections are used to connect the base to the patient marker or to the adapter, and the marker connections are used to connect the patient marker to the base or to the adapter.

4. The method of claim 1, wherein the detecting that the tip of the tool is in proximity to the accessible indicator comprises determining that the tip of the tool has been held on the accessible indicator for a preselected period of time.

5. The method of claim 1, wherein the detecting that the tip of the tool is in proximity to the accessible indicator comprises determining that the tip of the tool has been held in proximity to the accessible indicator for a preselected period of time.

6. The method of claim 1, wherein the detecting that the tip of the tool is in proximity to the accessible indicator comprises determining that the tip of the tool is within a preselected region.

7. The method of claim 1, further comprising repeating the calculating, determining, and checking, responsive to detecting that the tip of the tool is again in proximity to an accessible indicator of the at least one base indicator or the at least one adapter indicator.

8. The method of claim 7, further comprising, responsive to determining that another change in patient marker orientation has occurred, updating the registration to correspond to a new current patient marker orientation.

9. The method of claim 1, wherein the anchoring device comprises a clamp.

10. The method of claim 1, wherein the anchoring device comprises a pin.

* * * * *